US012586184B2

(12) United States Patent
Kwon et al.

(10) Patent No.: US 12,586,184 B2
(45) Date of Patent: Mar. 24, 2026

(54) METHODS AND APPARATUS FOR ANALYZING PATHOLOGY PATTERNS OF WHOLE-SLIDE IMAGES BASED ON GRAPH DEEP LEARNING

(71) Applicants: SEOUL NATIONAL UNIVERSITY R&DB FOUNDATION, Seoul (KR); SEOUL NATIONAL UNIVERSITY HOSPITAL, Seoul (KR)

(72) Inventors: Sunghoon Kwon, Seoul (KR); Yongju Lee, Goyang-si (KR); Kyoungseob Shin, Goyang-si (KR); Kyung Chul Moon, Seoul (KR); Jeong Hwan Park, Seoul (KR); Sohee Oh, Seoul (KR)

(73) Assignees: SEOUL NATIONAL UNIVERSITY R&DB FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 381 days.

(21) Appl. No.: 18/179,846

(22) Filed: Mar. 7, 2023

(65) Prior Publication Data

US 2023/0334662 A1     Oct. 19, 2023

(30) Foreign Application Priority Data

Mar. 8, 2022     (KR) ........................ 10-2022-0029619

(51) Int. Cl.
G06T 7/00 (2017.01)
A61B 8/00 (2006.01)
(Continued)

(52) U.S. Cl.
CPC .......... G06T 7/0012 (2013.01); A61B 8/5223 (2013.01); G06N 3/02 (2013.01);
(Continued)

(58) Field of Classification Search
CPC ..................... G06T 7/0012; G06T 7/11; G06T 2207/20084; G06T 2207/20072;
(Continued)

(56) References Cited

U.S. PATENT DOCUMENTS

2022/0084660 A1     3/2022   Georgescu et al.
2023/0177682 A1*    6/2023   Xiao ........................ G06T 7/11
                                                              382/133

FOREIGN PATENT DOCUMENTS

KR          20220012214 A     2/2022

OTHER PUBLICATIONS

Shoeleh et al., Graph based skill acquisition and transfer Learning for continuous reinforcement learning domains, online: Aug. 25, 2016 [retrieved Apr. 30, 2025], Pattern Recognition Letters, vol. 87, pp. 104-116. https://doi.org/10.1016/j.patrec.2016.08.009 (Year: 2016).*

(Continued)

*Primary Examiner* — Henok Shiferaw
*Assistant Examiner* — Dennis Rosario
(74) *Attorney, Agent, or Firm* — STIP Law Group, LLC

(57)                ABSTRACT

The present invention relates to a method and apparatus for analyzing pathology patterns of whole-slide images based on graph deep learning, which may include: a whole-slide image (WSI) compression step of compressing WSI into a superpatch graph; a graph neural networks (GNN) analysis step of embedding node features and context features into the superpatch graph through a GNN model and calculating contributions for each node and edge; a biomarker acquisition step of classifying and grouping the superpatch graph according to the contributions for each node, connecting the classified and grouped superpatch graph in units of groups to generate connected graphs, normalizing and clustering features of the connected graphs, and acquiring environmental graph biomarkers for each group; and a diagnostic informa-
(Continued)

tion extraction step of extracting and providing diagnostic information on the WSI based on the environmental graph biomarker for each group.

9 Claims, 22 Drawing Sheets

(51) Int. Cl.

| | |
|---|---|
| *G06N 3/02* | (2006.01) |
| *G06N 3/0464* | (2023.01) |
| *G06N 3/08* | (2023.01) |
| *G06N 5/04* | (2023.01) |
| *G06N 5/045* | (2023.01) |
| *G06N 7/01* | (2023.01) |
| *G06N 20/00* | (2019.01) |
| *G06T 7/10* | (2017.01) |
| *G06T 7/11* | (2017.01) |
| *G06T 7/162* | (2017.01) |
| *G06T 7/33* | (2017.01) |
| *G06V 10/26* | (2022.01) |
| *G06V 10/40* | (2022.01) |
| *G06V 10/426* | (2022.01) |
| *G06V 10/44* | (2022.01) |
| *G06V 10/50* | (2022.01) |
| *G06V 10/70* | (2022.01) |
| *G06V 10/762* | (2022.01) |
| *G06V 10/764* | (2022.01) |
| *G06V 10/82* | (2022.01) |
| *G06V 10/84* | (2022.01) |
| *G06V 20/40* | (2022.01) |
| *G06V 20/69* | (2022.01) |
| *G06V 40/12* | (2022.01) |
| *G16H 30/40* | (2018.01) |
| *G16H 50/00* | (2018.01) |
| *G16H 50/20* | (2018.01) |
| *G16H 50/30* | (2018.01) |

(52) U.S. Cl.
 CPC ............. *G06N 3/0464* (2023.01); *G06N 3/08* (2013.01); *G06N 5/04* (2013.01); *G06N 5/045* (2013.01); *G06N 7/01* (2023.01); *G06N 20/00* (2019.01); *G06T 7/10* (2017.01); *G06T 7/11* (2017.01); *G06T 7/162* (2017.01); *G06T 7/337* (2017.01); *G06V 10/26* (2022.01); *G06V 10/40* (2022.01); *G06V 10/426* (2022.01); *G06V 10/44* (2022.01); *G06V 10/50* (2022.01); *G06V 10/70* (2022.01); *G06V 10/762* (2022.01); *G06V 10/764* (2022.01); *G06V 10/82* (2022.01); *G06V 10/84* (2022.01); *G06V 20/46* (2022.01); *G06V 20/69* (2022.01); *G06V 20/695* (2022.01); *G06V 40/1347* (2022.01); *G16H 30/40* (2018.01); *G16H 50/00* (2018.01); *G16H 50/20* (2018.01); *G16H 50/30* (2018.01); *G06T 2207/10056* (2013.01); *G06T 2207/20021* (2013.01); *G06T 2207/20072* (2013.01); *G06T 2207/20081* (2013.01); *G06T 2207/20084* (2013.01); *G06T 2207/30004* (2013.01); *G06T 2207/30024* (2013.01); *G06T 2210/41* (2013.01); *G06V 2201/03* (2022.01)

(58) Field of Classification Search
 CPC ............. G06T 2207/30004; G06T 5/40; G06T 2210/41; G06T 2207/20081; G06T 2207/20021; G06T 7/10; G06T 7/162; G06T 2207/20112; G06T 7/248; G06T 2207/30024; G06T 2207/10056; G06T 7/337; G06T 5/60; G06V 10/44; G06V 10/762; G06V 10/764; G06V 10/454; G06V 10/7635; G06V 10/82; G06V 20/69; G06V 10/70; G06V 2201/03; G06V 20/695; G06V 10/26; G06V 10/40; G06V 10/42; G06V 10/426; G06V 20/46; G06V 40/171; G06V 20/693; G06V 10/84; G06V 10/86; G06V 10/421; G06V 20/49; G06V 20/00; G06V 2201/122; G06V 40/382; G06V 10/77; G06V 10/7715; G06V 10/771; G06V 10/806; G06V 10/50; G06V 20/698; G06V 40/1347; G16H 50/20; G16H 50/30; G16H 30/40; G16H 50/00; G16H 70/60; G06N 3/08; G06N 20/00; G06N 5/04; G06N 3/082; G06N 5/045; G06N 7/01; G06N 3/02; G06N 3/0464; A61B 8/5207; A61B 8/5223; A61B 8/52; A61B 90/20
 See application file for complete search history.

(56) References Cited

OTHER PUBLICATIONS

Abu-El-Haija et al., N-GCN: Multi-scale Graph Convolution for Semi-supervised Node Classification, Feb. 24, 2018 [retrieved Feb. 24, 2018], Cornell University:arXix, version [v1], 9 pages. https://doi.org/10.48550/arXiv.1802.08888 (Year: 2018).*

Li, Adaptive Graph Convolutional Neural Network and Its Biomedical Applications (dissertation), 2020 [ retrieved Apr. 30, 2025], The University of Texas at Arligton, 104 pages. https://mavmatrix.uta.edu/cse_dissertations/358 (Year: 2020).*

Zormpas-Petridis et al., SuperHistopath: A Deep Learning Pipeline for Mapping Tumor Heterogeneity on Low-Resolution Whole-Slide Digital Histopathology Images, Jan. 19, 2021 [retrieved Apr. 30, 2025], Frontiers in Oncology, vol. 10, pp. 1-13. https://doi.org/10.3389/fonc.2020.586292 (Year: 2021).*

Lee et al., Derivation of prognostic contextual histopathological features from whole-slide images of tumours via graph deep learning, Aug. 18, 2022 [STIC retrieved Apr. 28, 2025], nature biomedical engineering, 29 pages. https://doi.org/10.1038/s41551-022-00923-0 (Year: 2022).*

Yongju Lee, Prognosis Prediction of Cancer Patients and Discovery of Cancer Microenvironment Biomarkers Using Graph Neural Network (dissertation), Aug. 2022 [retrieved Apr. 30, 2025], Seoul National University, 88 pages. https://hdl.handle.net/10371/187740 (Year: 2022).*

Google Patents machine translation of IDS cited KR 2022-0012214 A to 제오르제스쿠 (Georgescu) et al., Artificial Intelligence Processing Systems and Automated Pre-Diagnostic Workflows for Digital Pathology, translated May 1, 2025, 22 pages. (Year: 2025).*

Mueller et al., Visual Object Categorization Based on Hierarchical Shape Motifs Learned From Noisy Point Cloud Decompositions, May 9, 2019 [retrieved Sep. 28, 2025], Journal of Intelligent & Robotic Systems, vol. 97, pp. 313-338. DOI https://doi.org/10.1007/s10846-019-01016-y (Year: 2019).*

Ge et al., A Peek Into the Reasoning of Neural Networks: Interpreting with Structural Visual Concepts, May 1, 2021 [retrieved Sep. 28, 2025], Cornell University: arXiv, version: [v1], 11 pages. https://doi.org/10.48550/arXiv.2105.00290 (Year: 2021).*

Ding et al., Graph Convolutional Networks for Multi-modality Medical Imaging: Methods, Architectures, and Clinical Applications, Feb. 17, 2022 [retrieved Sep. 28, 2025], Cornell University: arXiv, version: [v1], 42 pages. https://doi.org/10.48550/arXiv.2202.08916 (Year: 2022).*

* cited by examiner

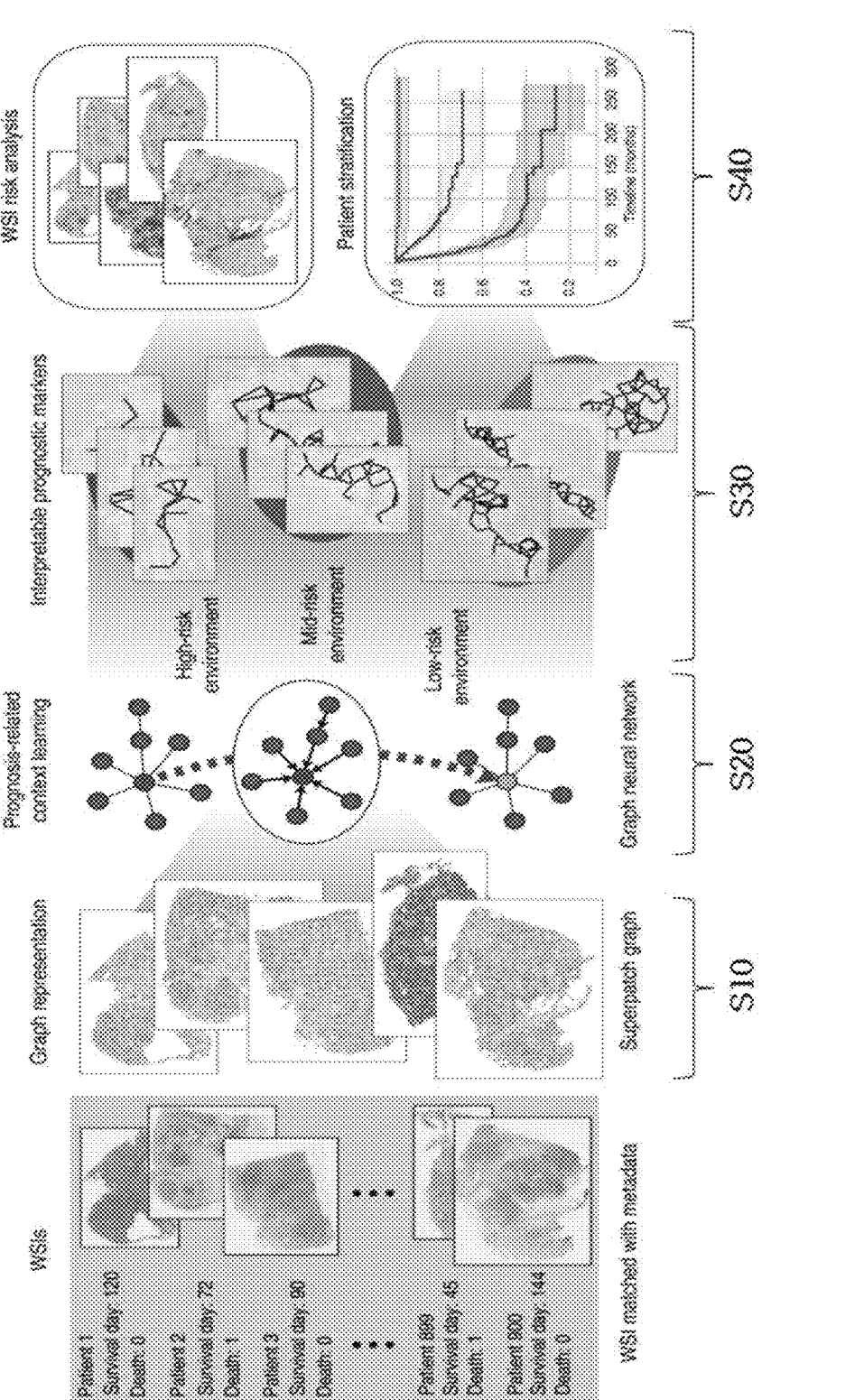
[FIG. 1]

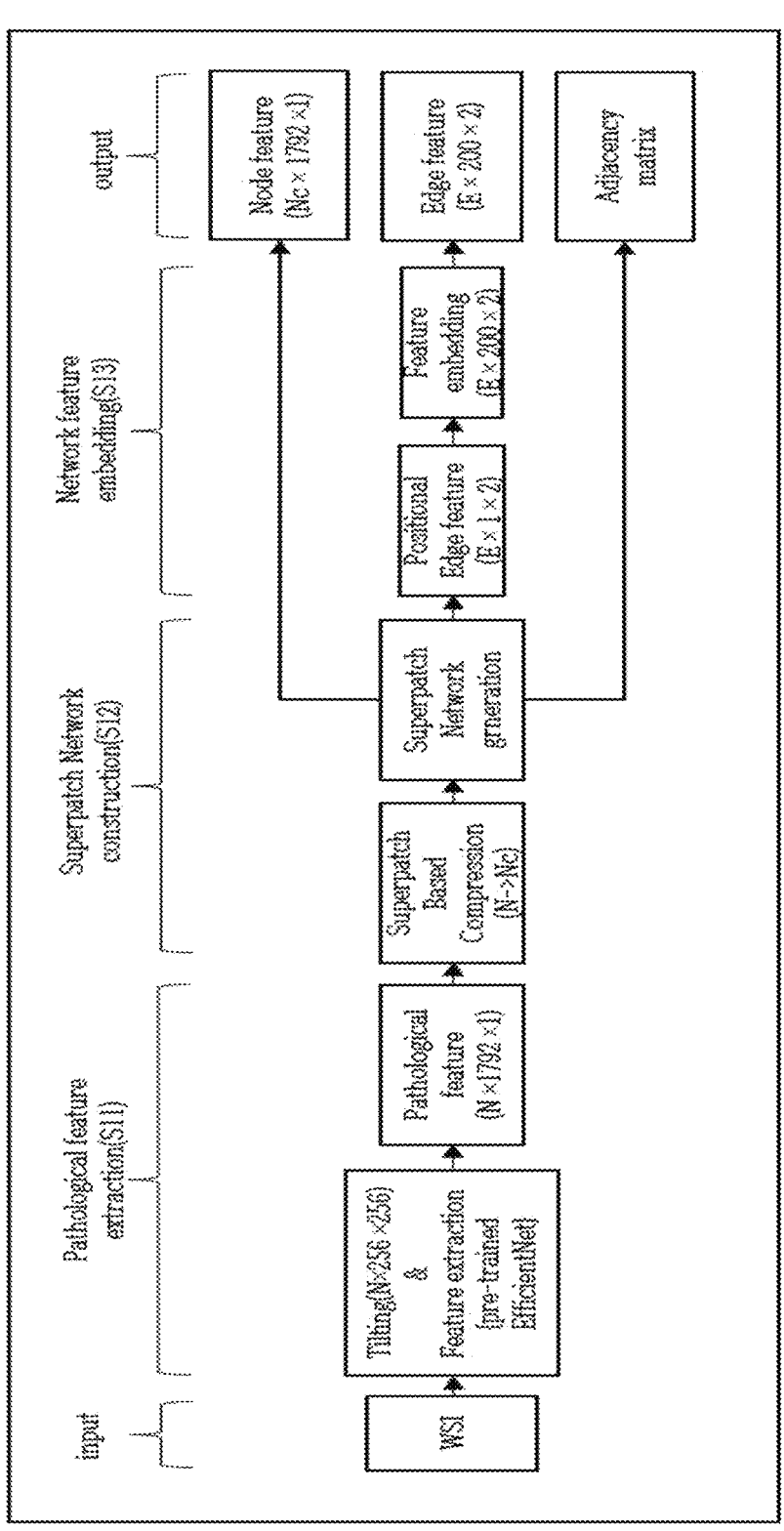
[FIG. 2]

[FIG. 3]
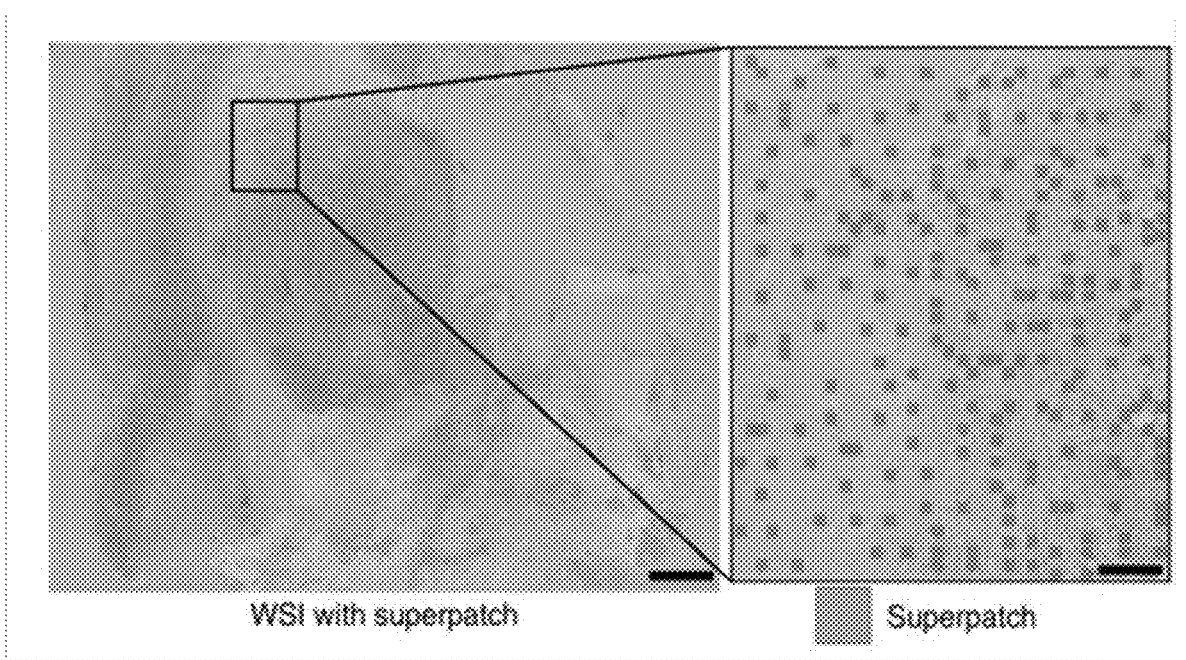
WSI with superpatch                    Superpatch
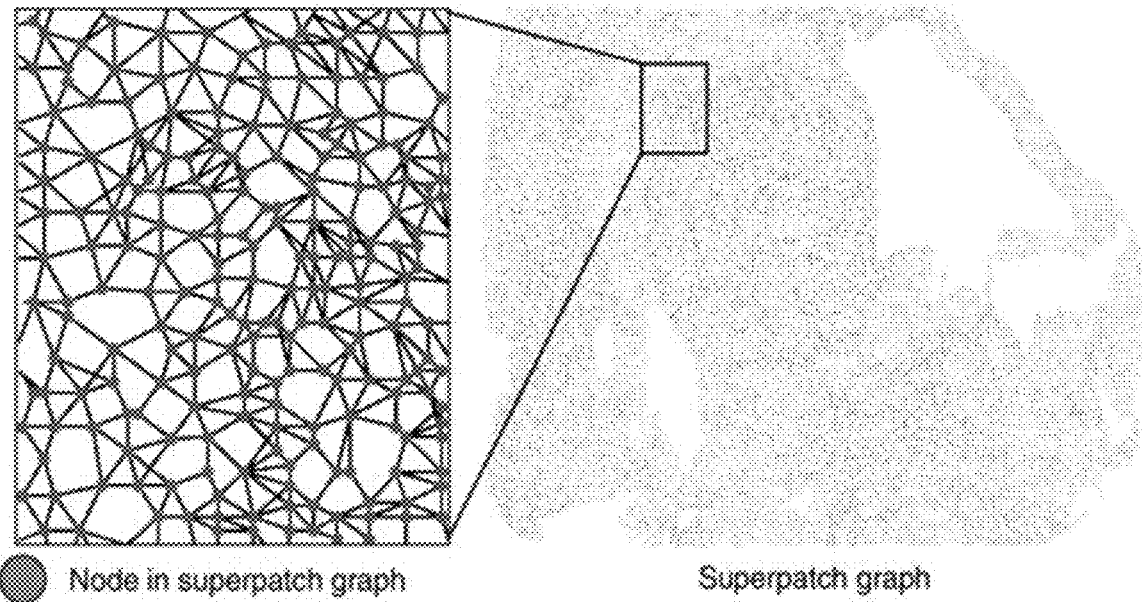
Node in superpatch graph          Superpatch graph

[FIG. 4]
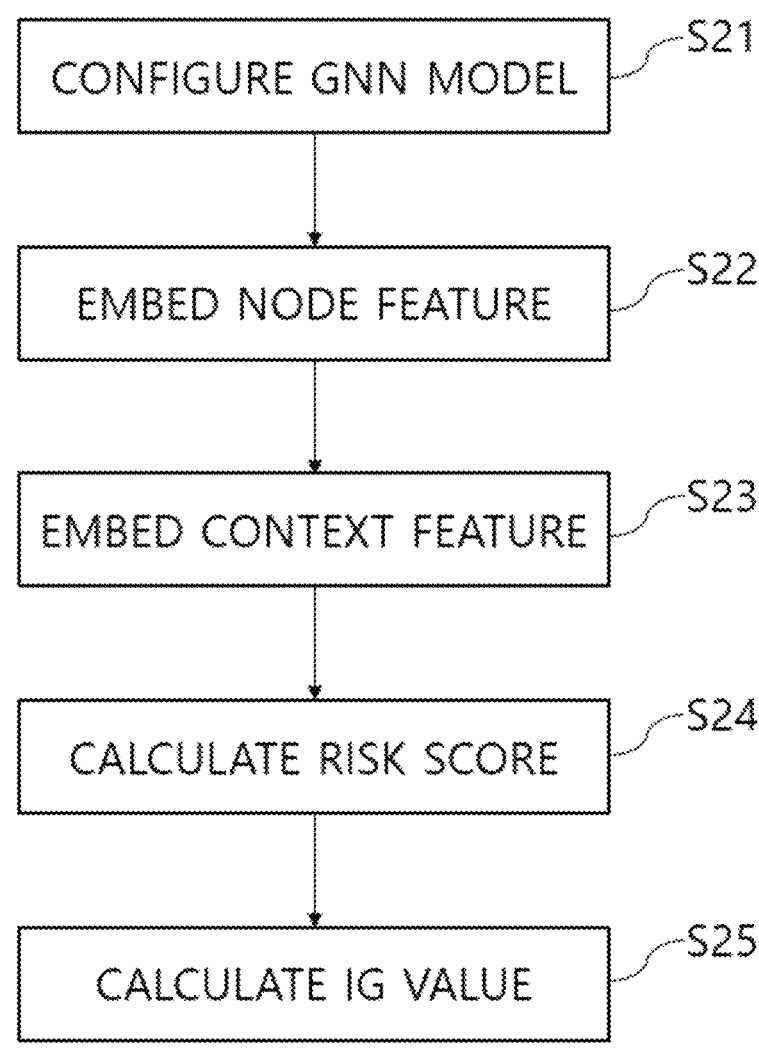

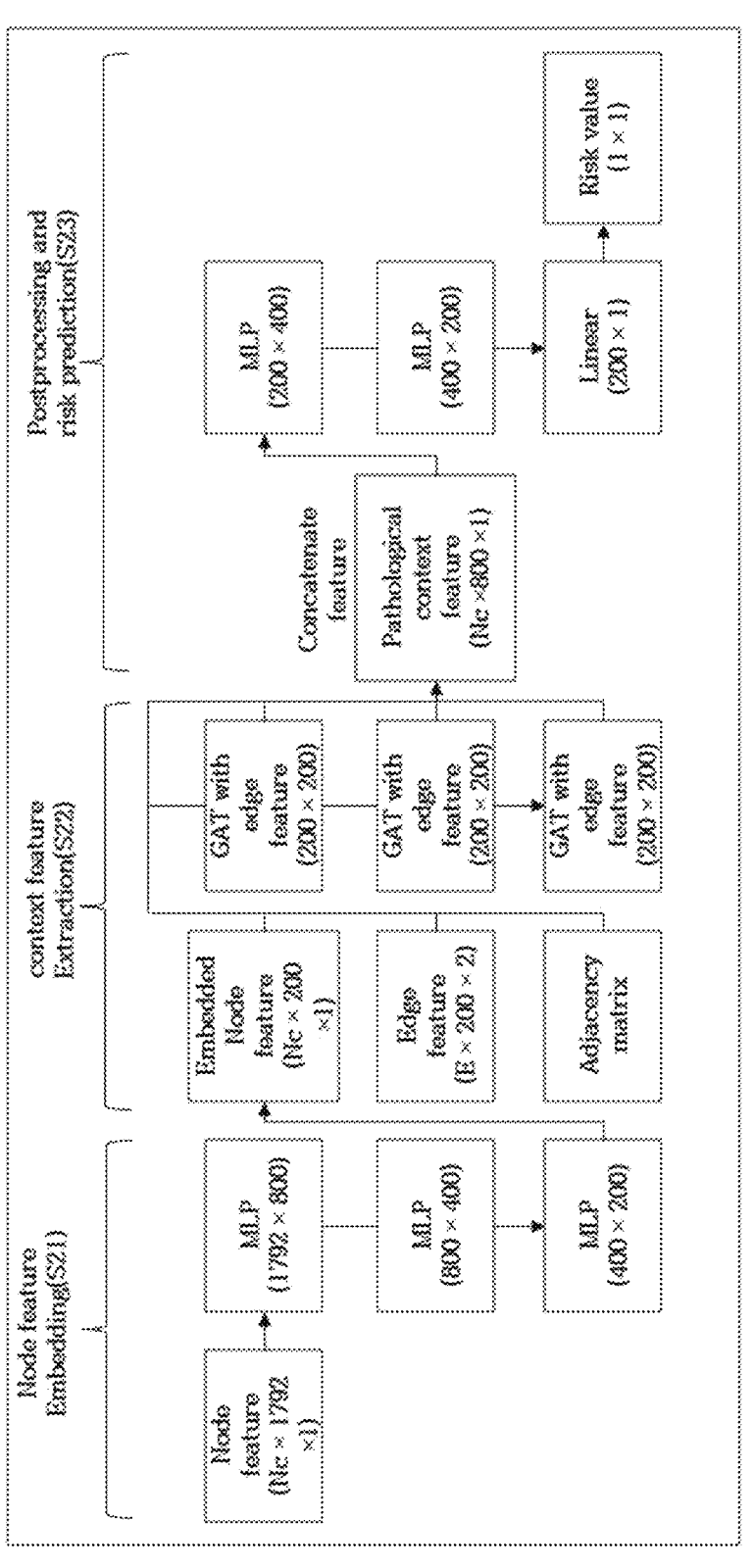
[FIG. 5]

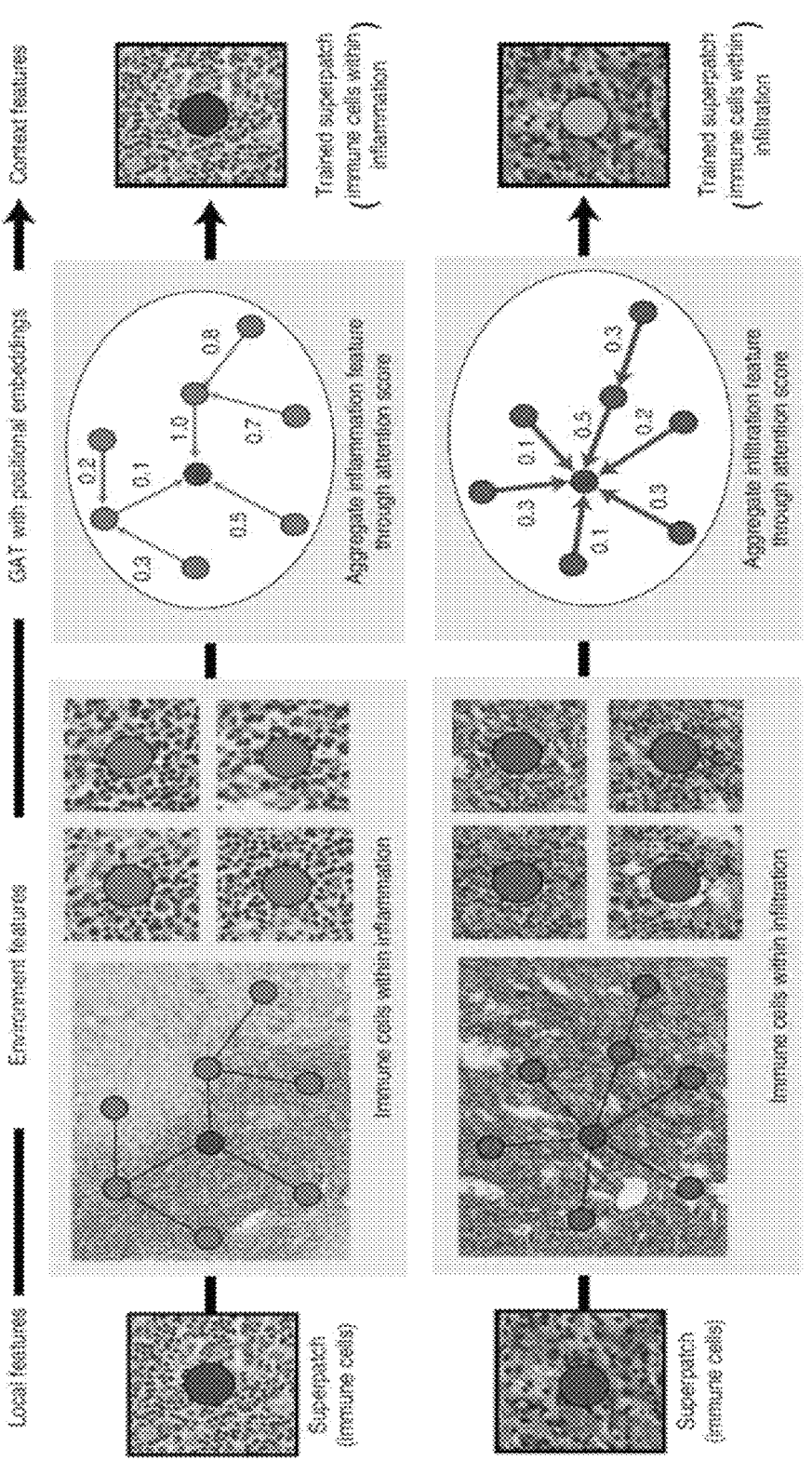
[FIG. 6]

[FIG. 7]
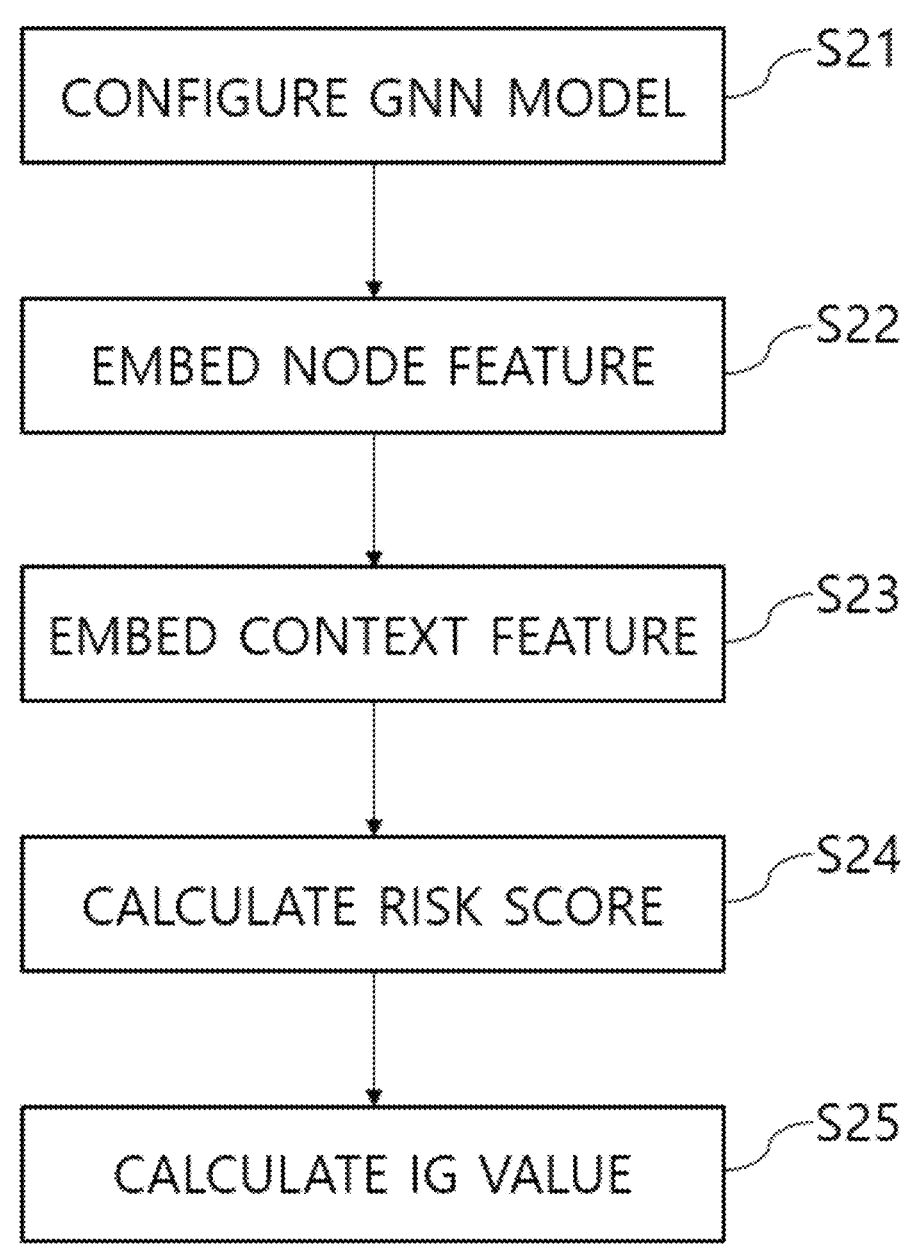

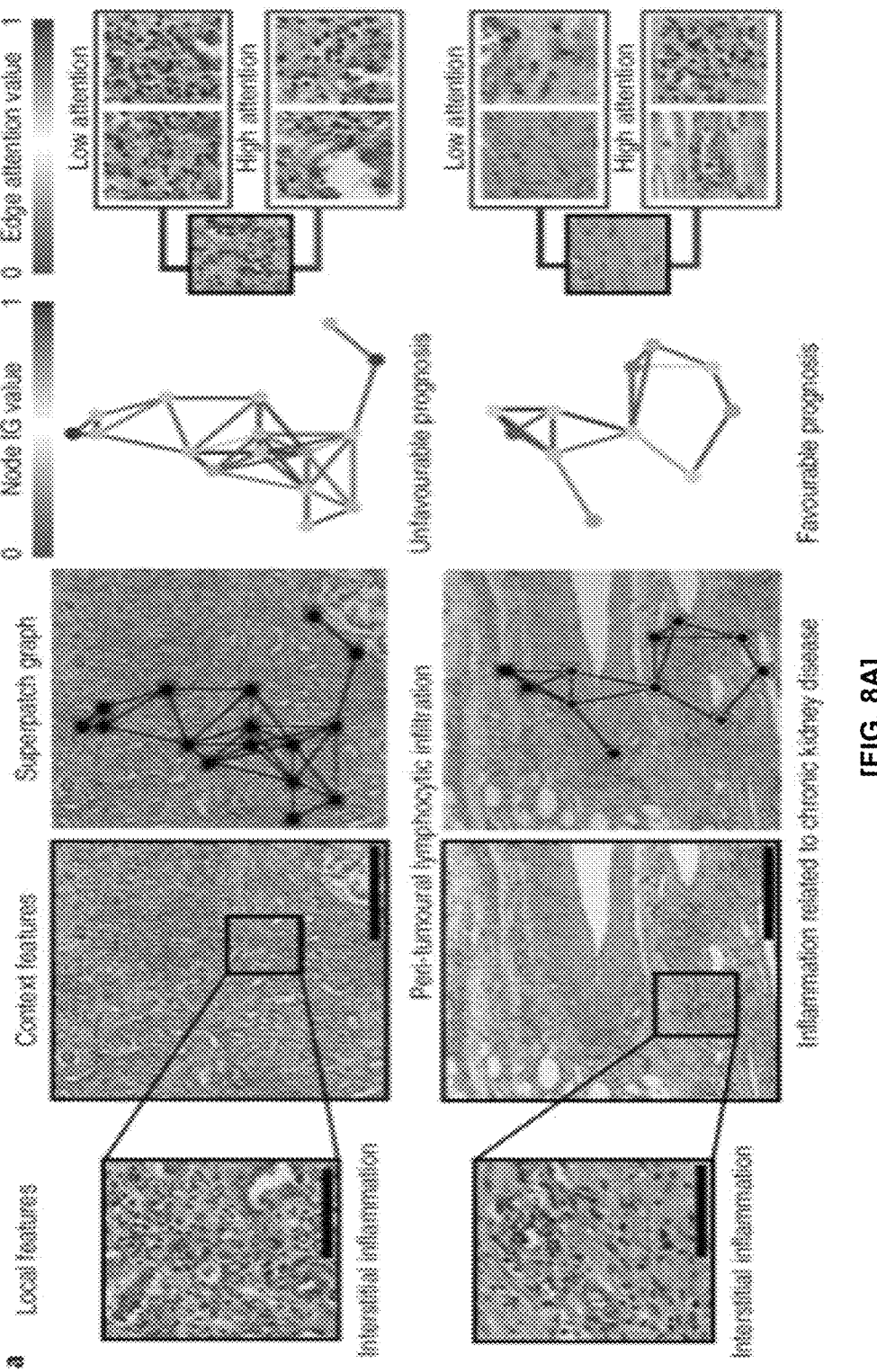
[FIG. 8A]

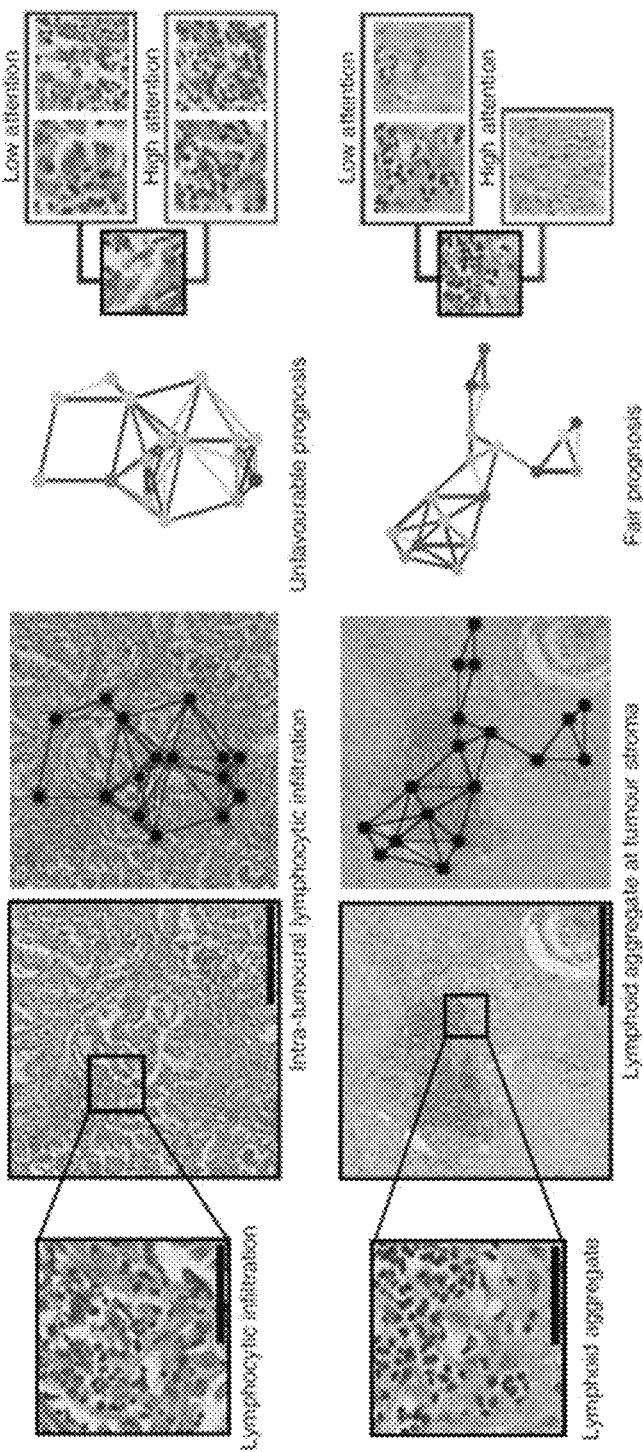
[FIG. 8B]

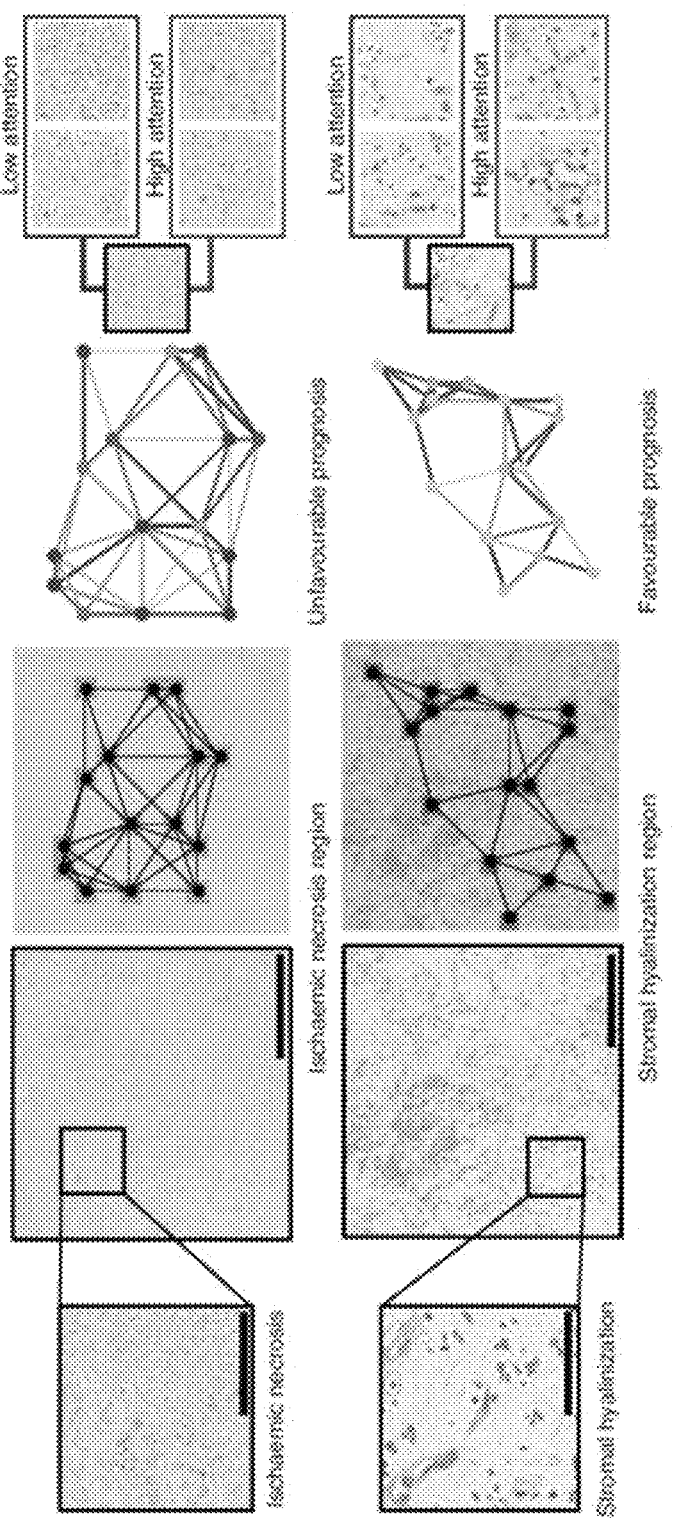
[FIG. 8C]

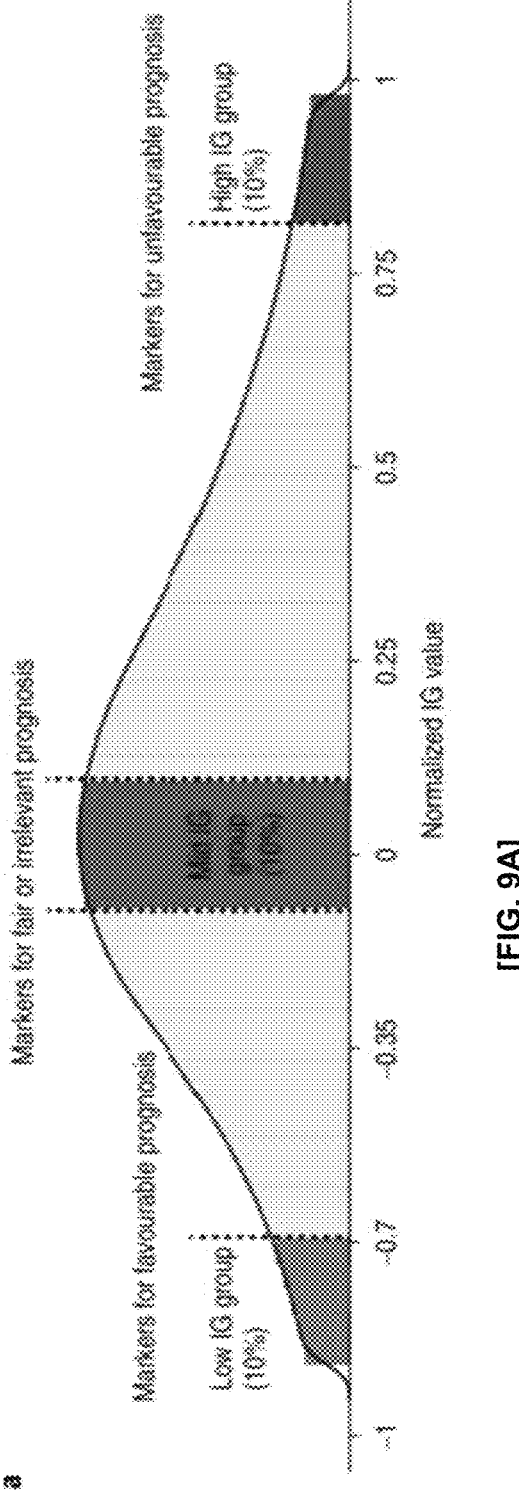
[FIG. 9A]

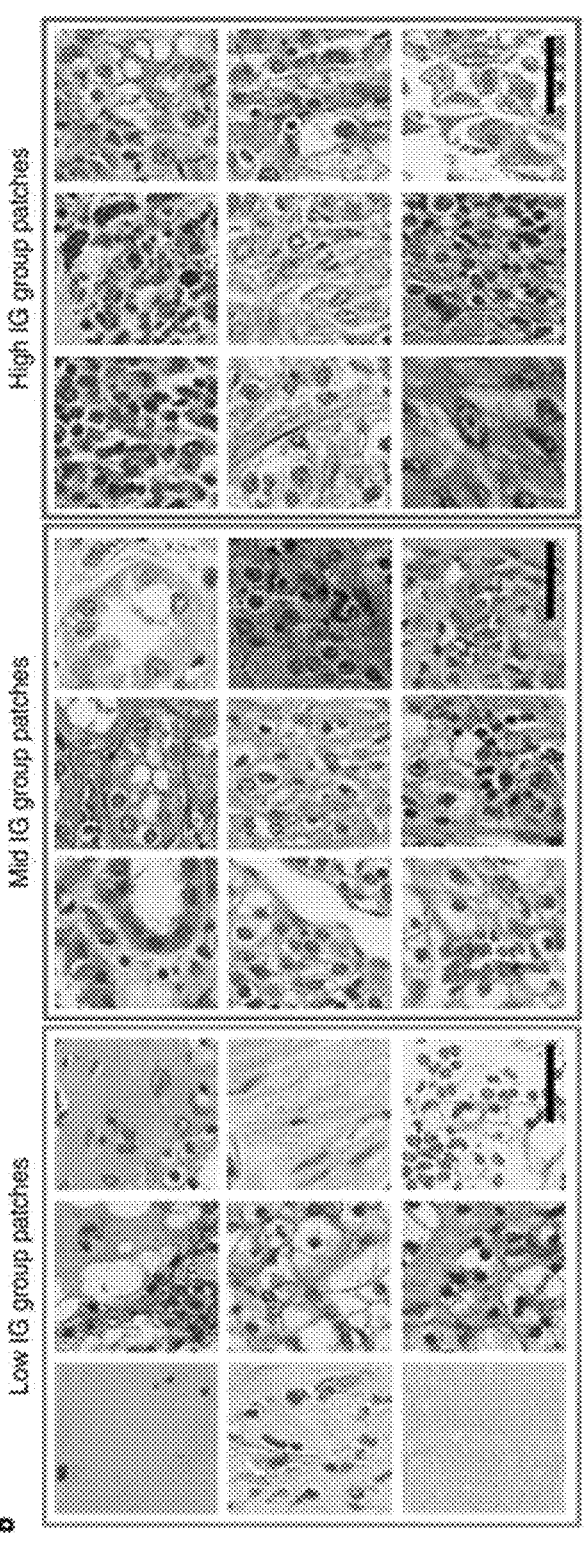
[FIG. 9B]

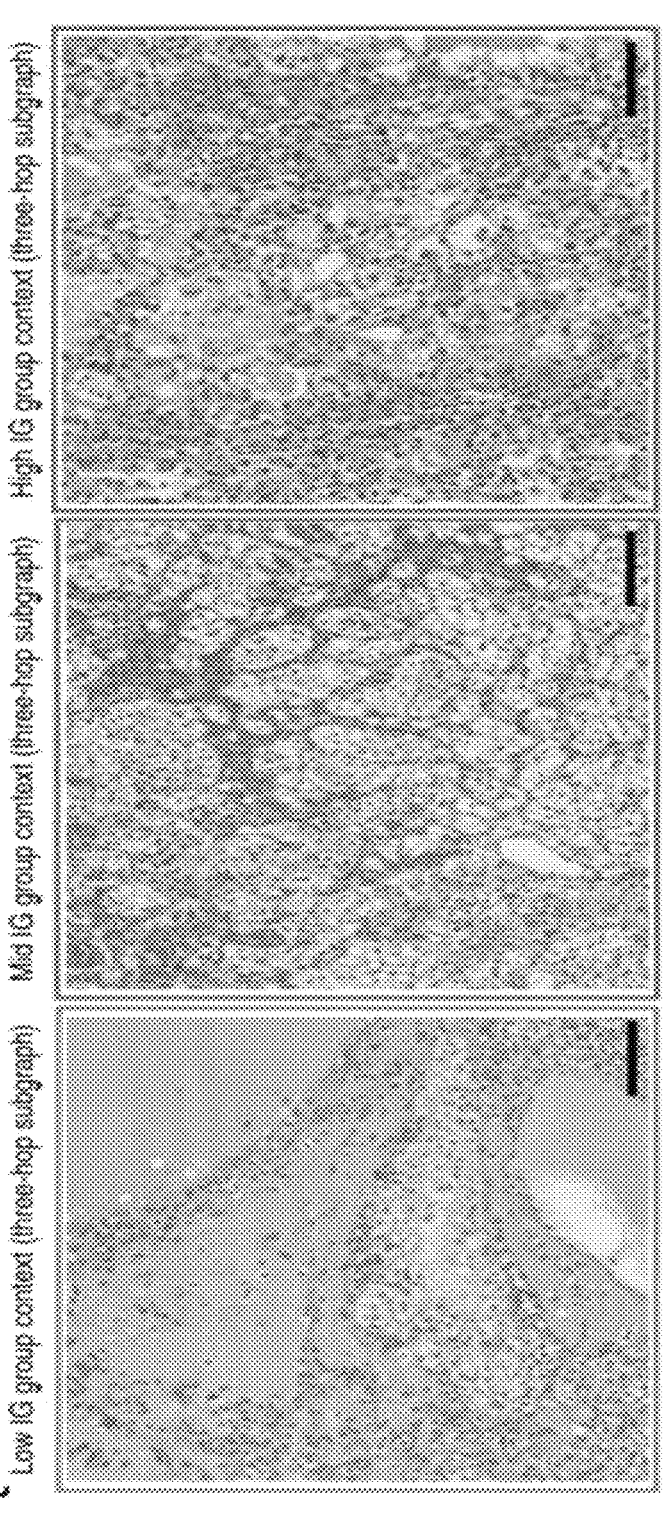
[FIG. 9C]

[FIG. 10]
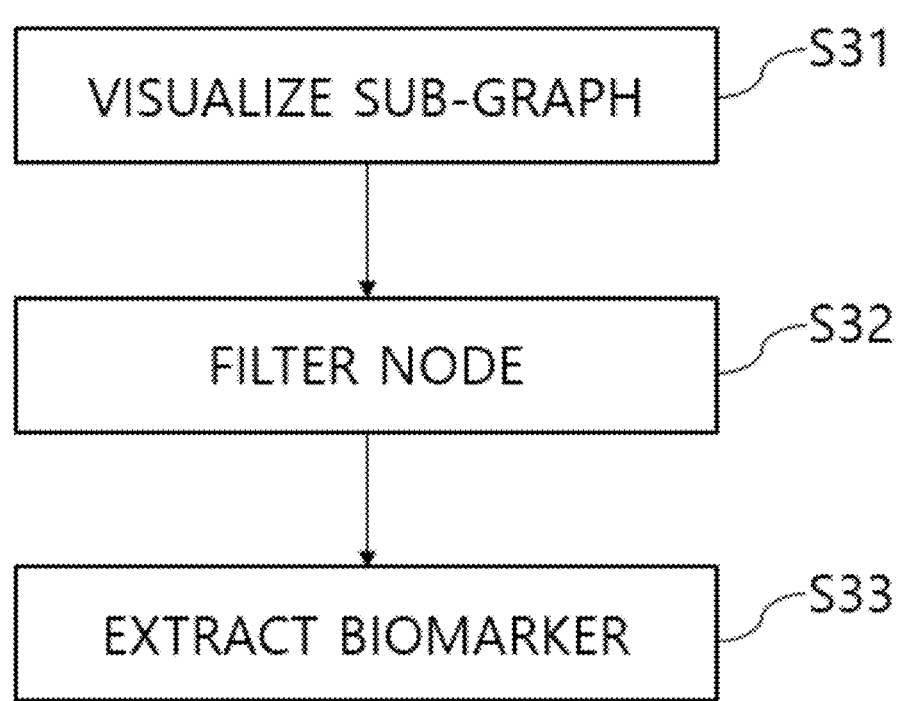

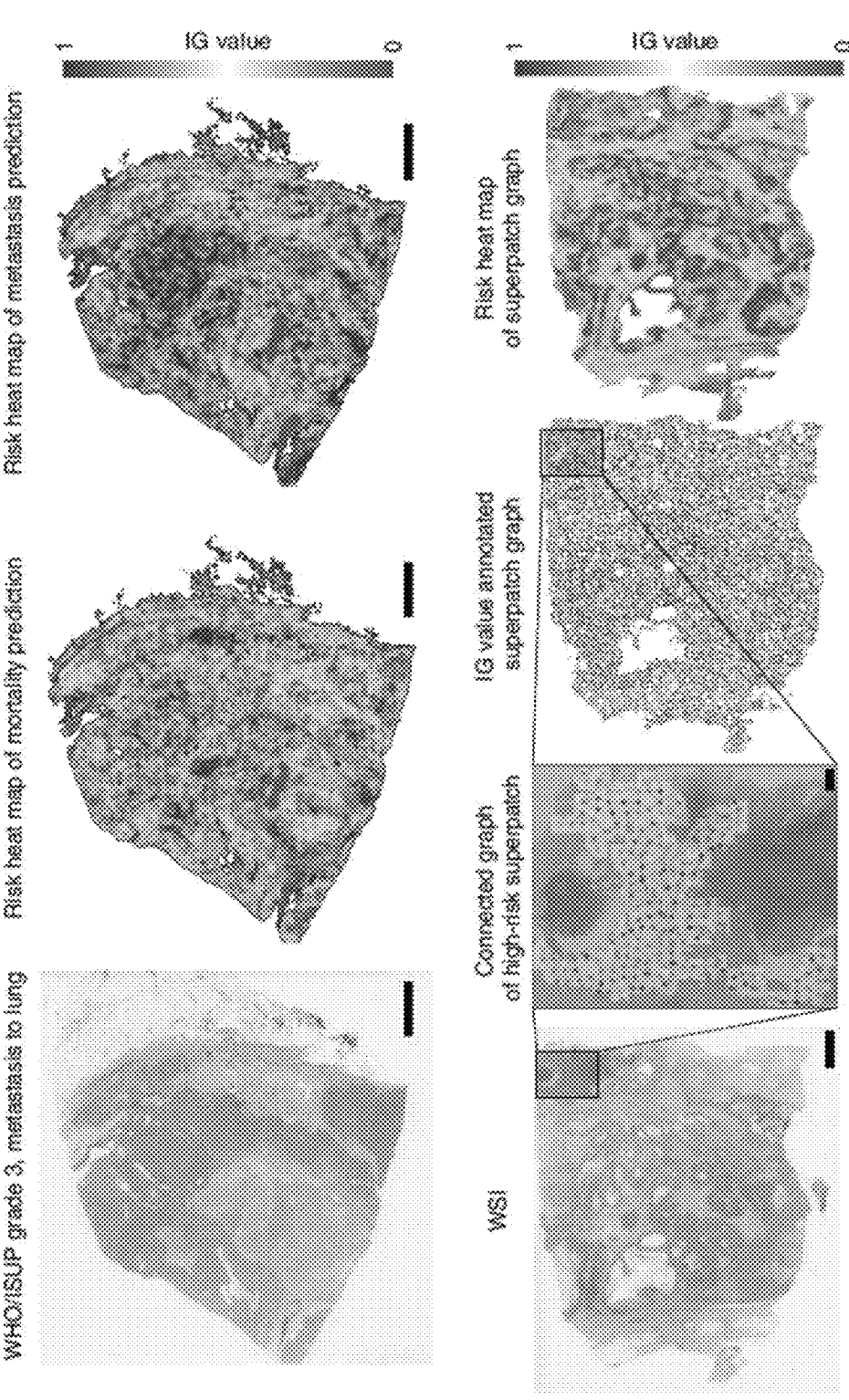
[FIG.11]

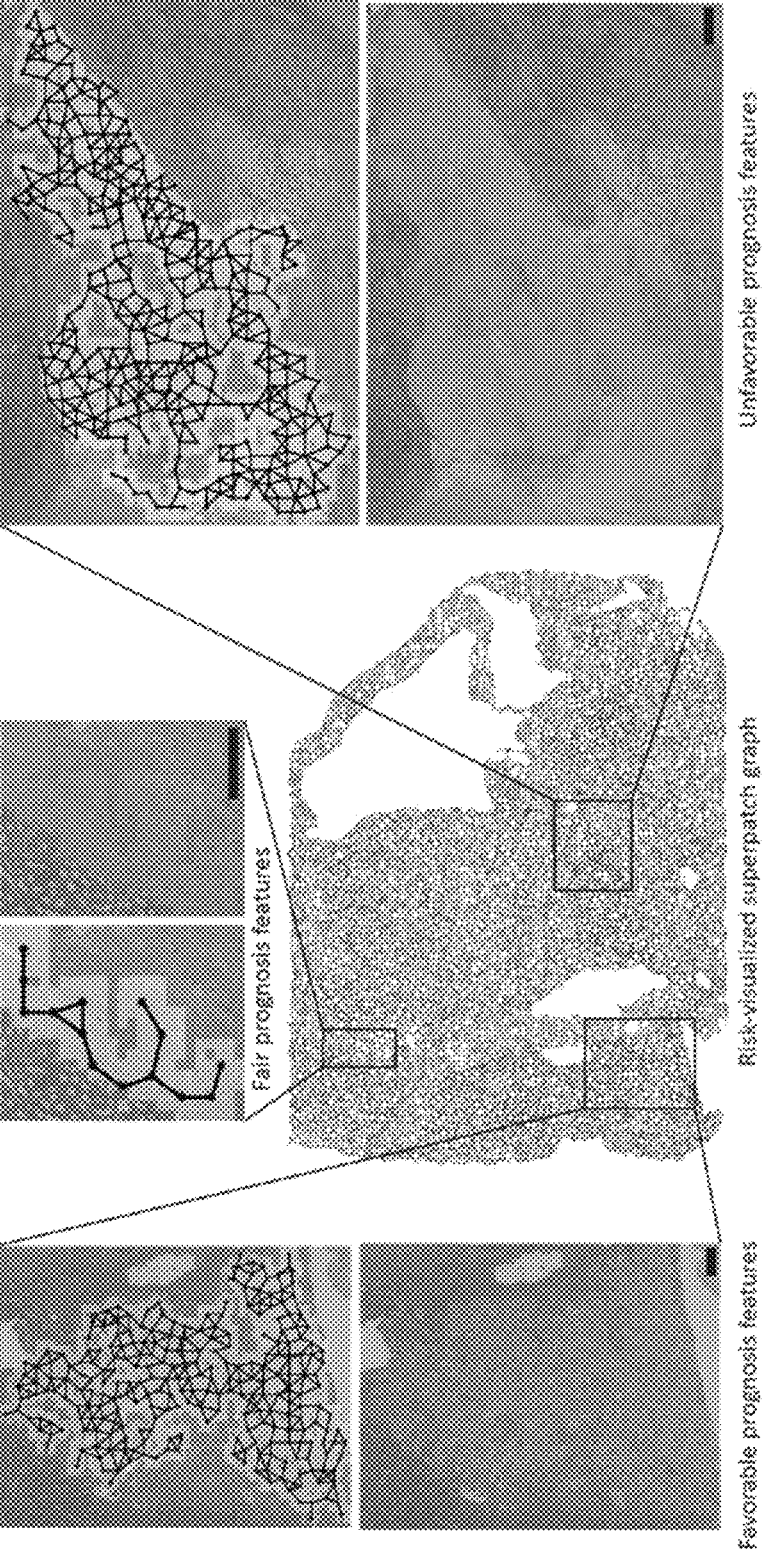
[FIG. 12]

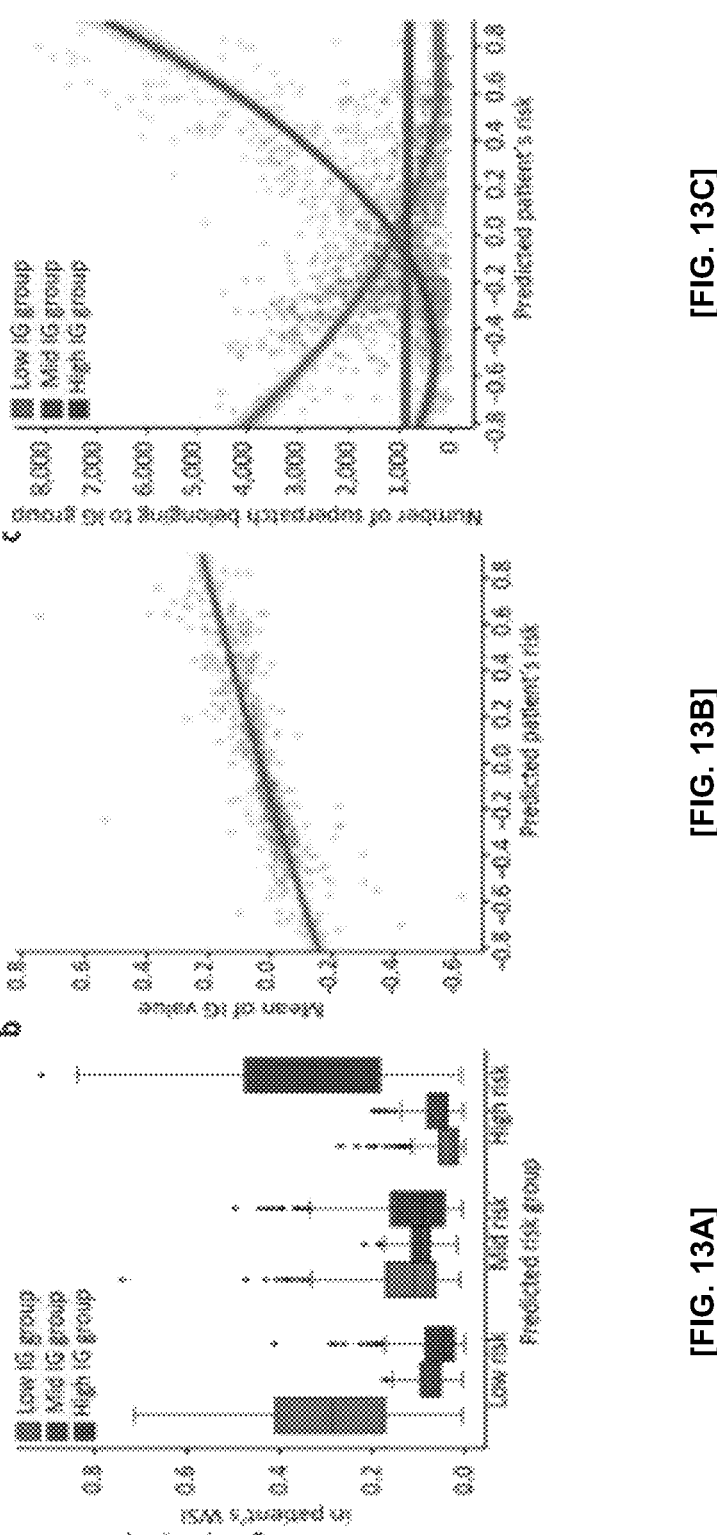
[FIG. 13C]
[FIG. 13B]
[FIG. 13A]

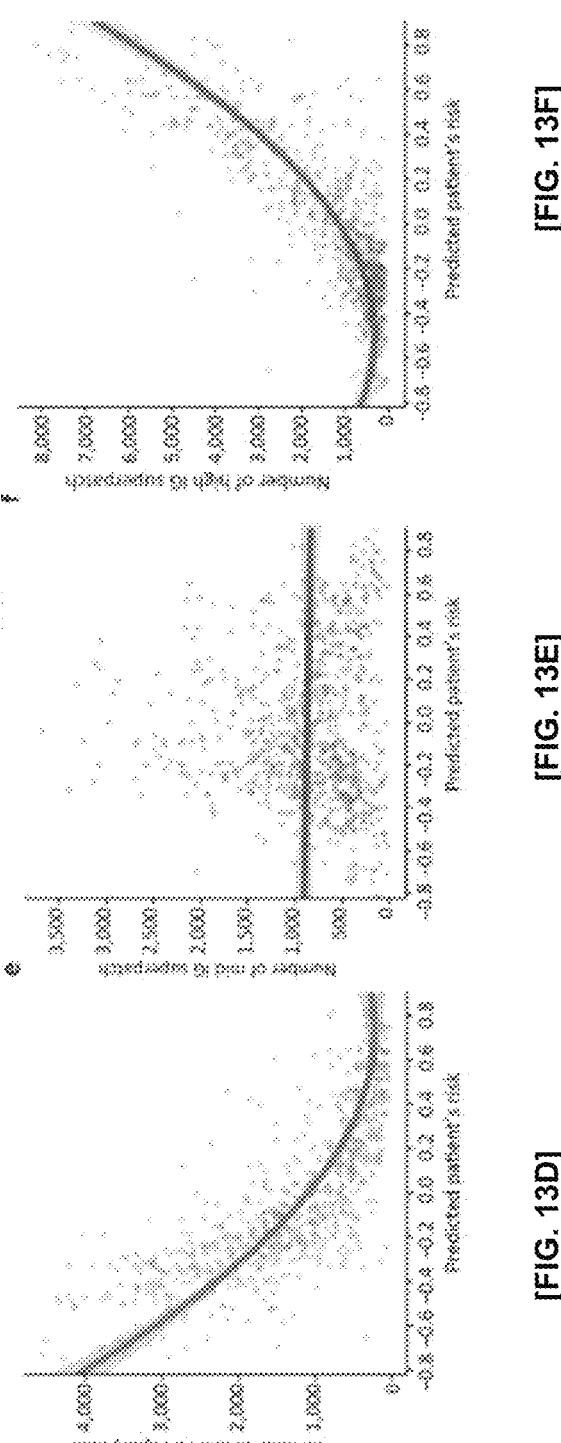
[FIG. 13F]
[FIG. 13E]
[FIG. 13D]

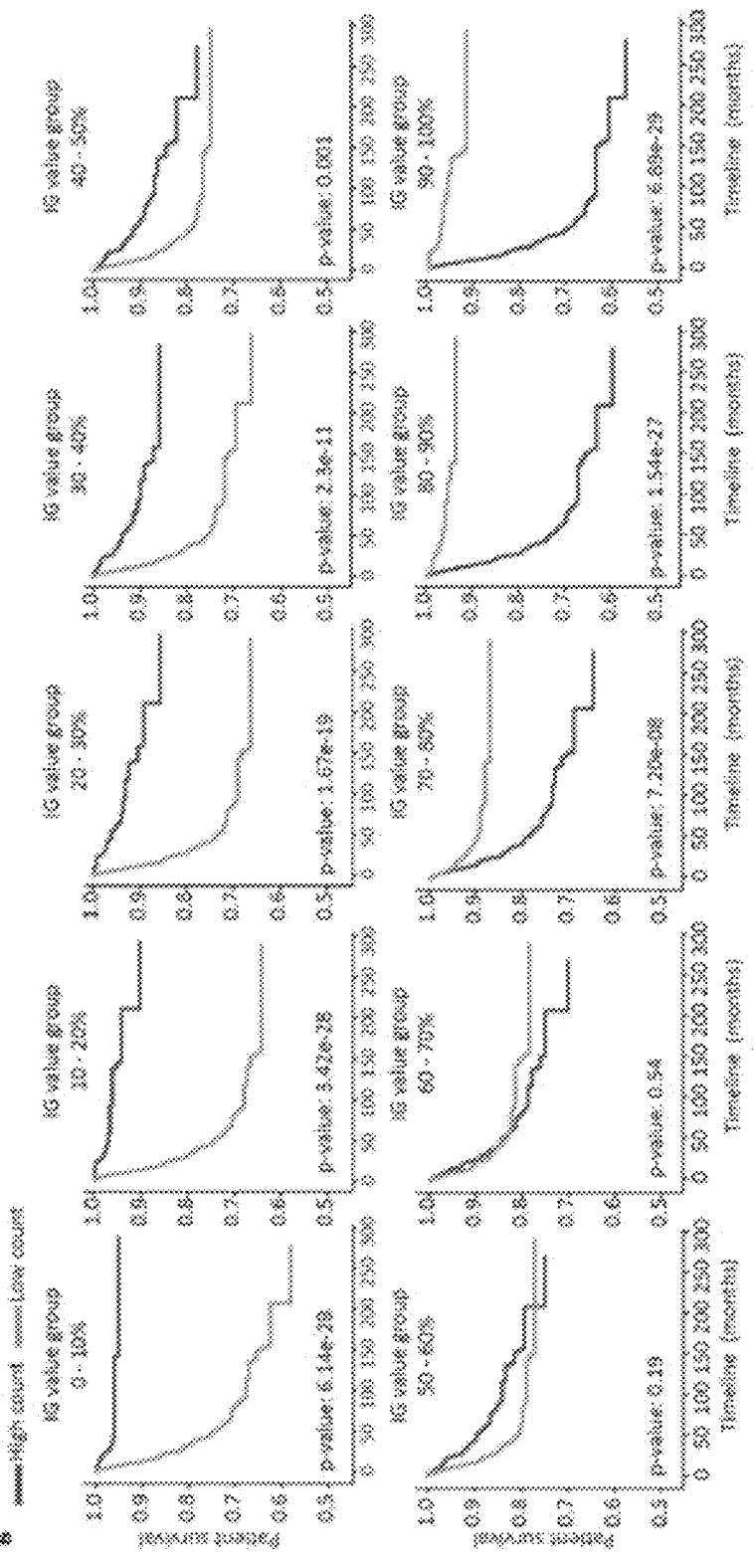
[FIG. 13G]

[FIG. 14]
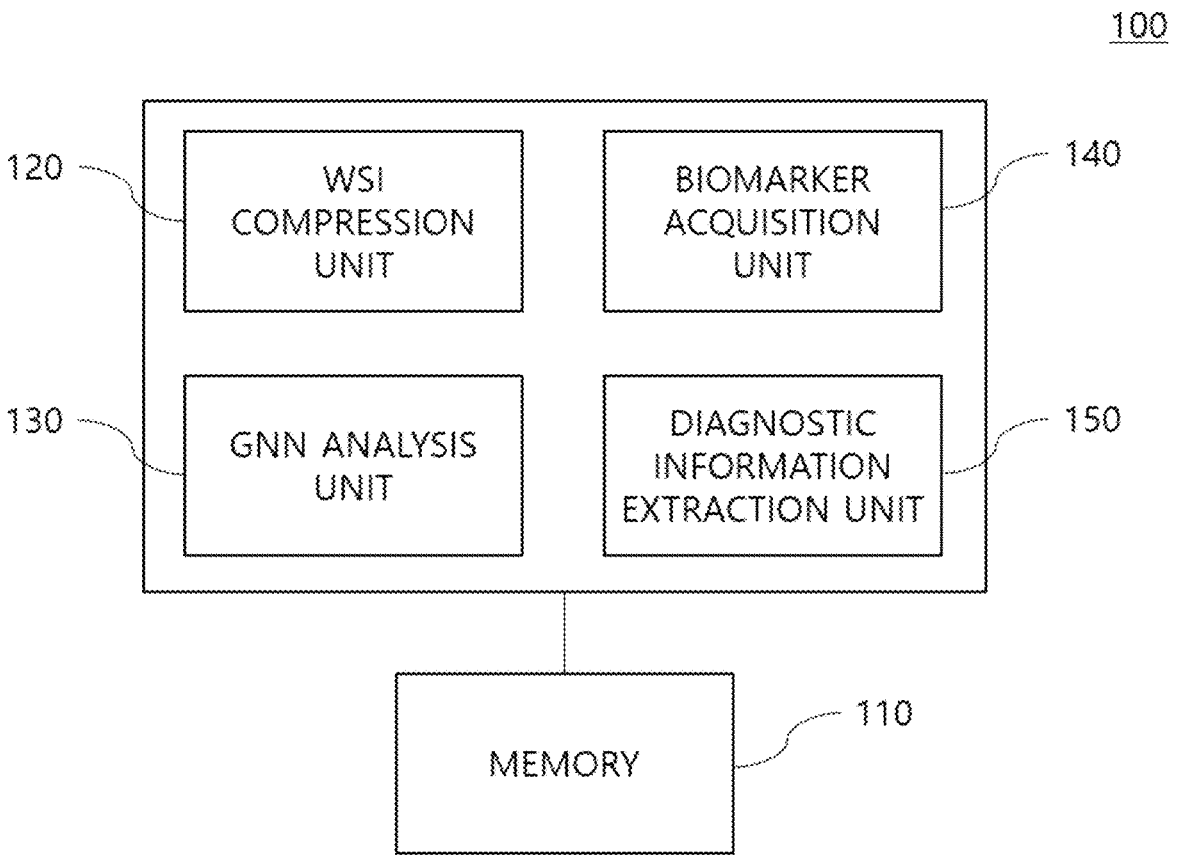

[FIG. 15A]
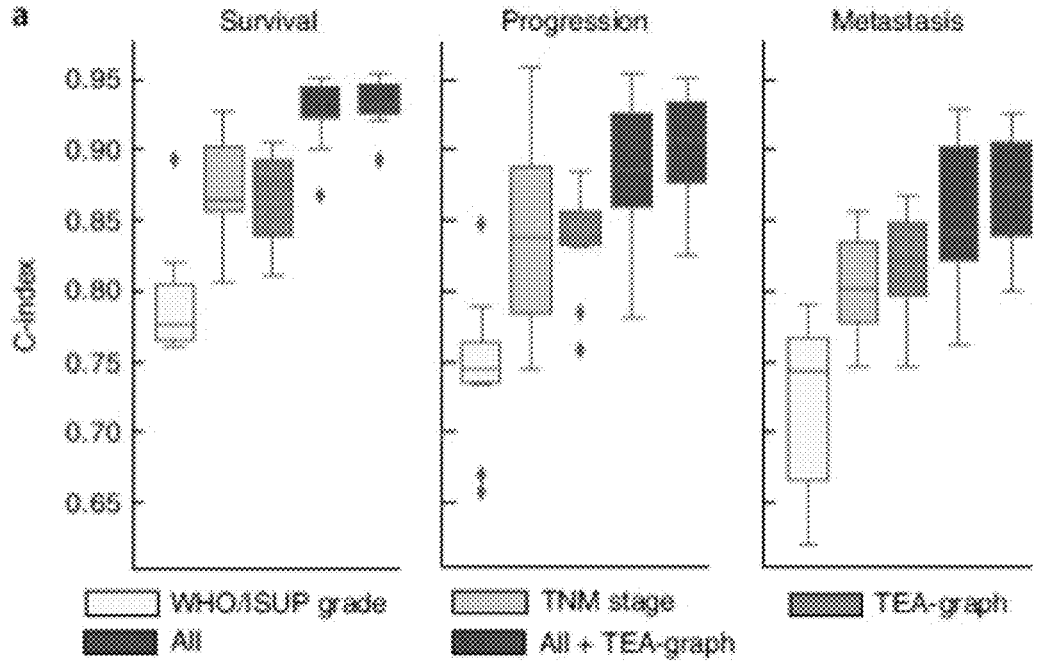
[FIG. 15B]
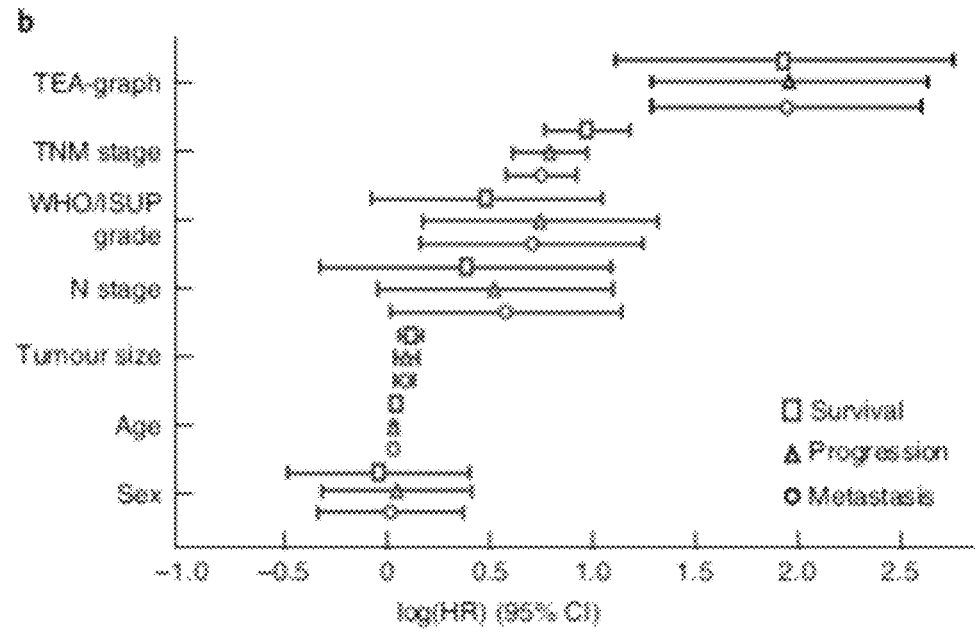

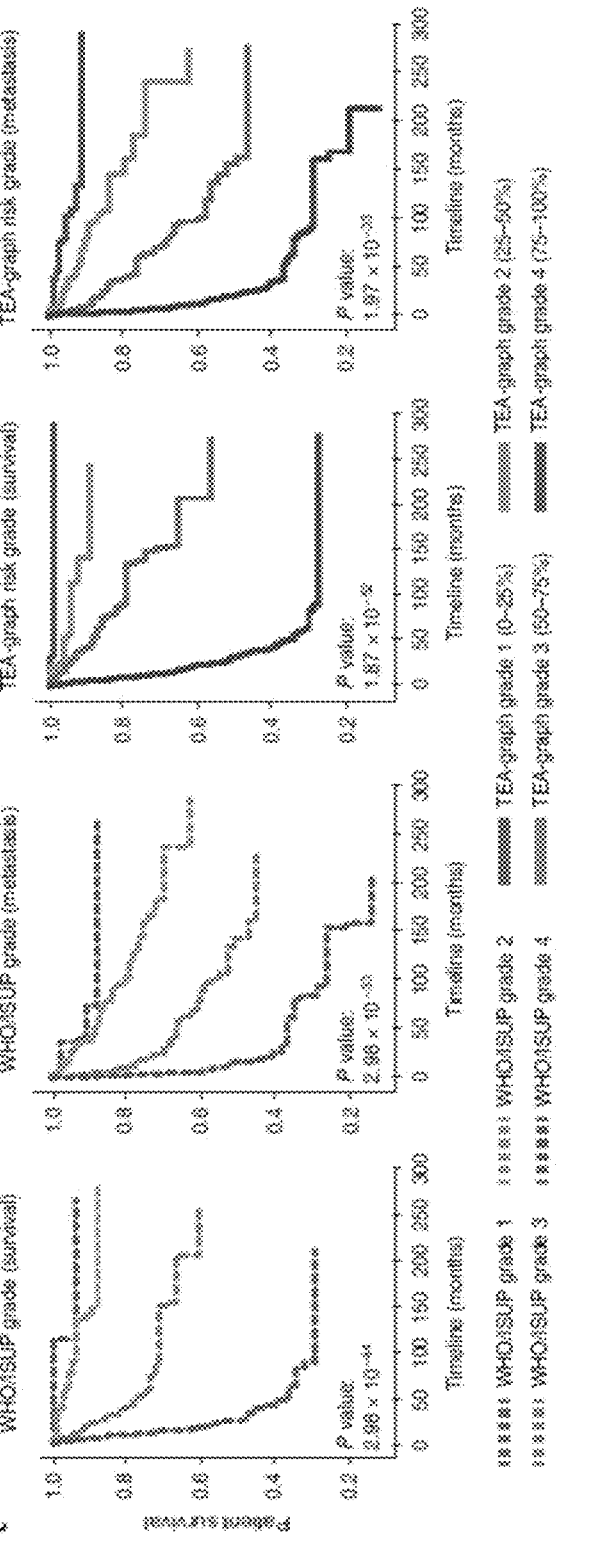
[FIG. 15C]

METHODS AND APPARATUS FOR ANALYZING PATHOLOGY PATTERNS OF WHOLE-SLIDE IMAGES BASED ON GRAPH DEEP LEARNING

BACKGROUND

(a) Technical Field

The present invention relates to a method and apparatus for analyzing pathology patterns of whole-slide images based on graph deep learning, which can acquire and provide various types of information enabling analysis of pathology patterns from whole-slide images through graph deep learning.

(b) Background Art

Existing pathology analysis is performed in a way in which pathologists with specialized knowledge observe, analyze, and report cancer tissues individually through a microscope, which is a labor-intensive process for pathologists to conduct analysis. Recently, with the advent of digital pathology technology that may digitize and analyze cancer tissues with high-resolution images composed of gigapixels, various algorithms that may relieve the burden of pathologists and be applied to pathological images have been developed. Among these algorithms, in particular, an algorithm using a neural network showed excellent performance.

A convolutional neural network (CNN), which recognizes and learns patterns in units of pixels located close to each other, diagnoses cancer, predicts patient's prognosis, and furthermore, predicts gene mutations and gene expression levels in cancer tissues.

However, the deep learning algorithms have limitations in that they may not reflect both heterogeneity of cancer tissues and characteristics of the tumor microenvironment in the whole high-resolution pathology image of gigapixels.

Due to these limitations, it was not possible to confirm patterns of cancer tissues learned through the deep learning algorithm in a form that can be reinterpreted by humans at the levels of the whole pathology images.

In order for the deep learning algorithm to be used in the actual medical field, the deep learning algorithm not only has good predictive performance, but also should allow medical professionals to see and determine which patterns play a significant role in their predictions and confirm that these patterns are applicable to patients.

Conventionally, it was possible to interpret patterns of pathology images by using an interpretable CNN model, but when the heterogeneity of the cancer tissues sporadically and variously exists throughout the pathology images, there are inherent limitations to the interpretation of the pathology patterns using the CNN model.

Accordingly, the present invention provides a methodology which can learn heterogeneous patterns in cancer tissue that determines patient's prognosis and success or failure of a treatment, even in all of high-resolution pathological images of gigapixels, as in the above example, and can also be used in the actual medical field and furthermore used to discover pathology-based diagnostic markers by presenting heterogeneous patterns on pathological images learned by a model to be interpretable.

PRIOR ART DOCUMENT

Patent Document

Korean Laid-open Patent Publication No. 10-2022-0012214 (published on Feb. 3, 2022)

SUMMARY OF THE INVENTION

The present invention is intended to provide a new method and apparatus for analyzing pathology patterns of whole-slide images based on graph deep learning capable of compressing large-capacity whole-slide images, and acquiring and providing various types of information enabling pathology pattern analysis through the graph deep learning.

According to an aspect of the present invention, a method of analyzing pathology patterns of whole-slide images (WSI) based on graph deep learning includes: a whole-slide image (WSI) compression step of compressing WSI into a superpatch graph; a graph neural networks (GNN) analysis step of embedding node features and context features into the superpatch graph through a GNN model and calculating contributions for each node and edge; a biomarker acquisition step of classifying and grouping the superpatch graph according to the contributions for each node, connecting the classified and grouped superpatch graph in units of groups to generate connected graphs, normalizing and clustering features of the connected graphs, and acquiring environmental graph biomarkers for each group; and a diagnostic information extraction step of extracting and providing diagnostic information on the WSI based on the environmental graph biomarker for each group.

The WSI compression step may include: segmenting the WSI into N small patches; generating the superpatch graph according to a similarity of the small patches, and then using the superpatch as a node and connecting between the superpatches with an edge to graph the superpatch graph; and integrating features of the small patches in units of superpatches to calculate node features for each superpatch, and calculating edge features through spatial information between the superpatches.

The GNN model may have a function of calculating contributions for each edge to reflect a heterogeneous surrounding environment feature to a context feature and a function of calculating the contributions for each edge, including spatial information between the superpatches, to promote location information transfer between the superpatches.

The spatial information between the superpatches may include a distance and an angle between the superpatches.

The GNN analysis step may include the steps of: reducing a vector dimension of the node features for each superpatch; embedding the node features and the context features in the superpatch graph through the GNN model; extracting the context features through the GNN model and calculating a risk score; and calculating the IG value of each node, thereby calculating a contribution between adjacent superpatches, including spatial information between the superpatches, to reflect a heterogeneous surrounding environment feature to the context feature.

The biomarker acquisition step may include the steps of: generating and displaying subgraphs by connecting between the superpatches with the edge using the superpatch as a node and additionally guiding at least one of contributions for each node and contributions for each edge; classifying and grouping the subgraphs according to the contributions for each node, and then connecting the classified and grouped subgraphs in the units of groups to generate the connected graphs, and averaging all the node features in the connected graph to define connected graph features; and normalizing and clustering all the connected graph features within the same group to extract biomarkers of each group.

In the step of defining the connected graph features, only graphs having a predetermined number of nodes or more among largest connected graphs within the same group may be defined as the connected graph.

The risk analysis step may include: detecting and notifying the risk in the WSI based on a connectivity analysis result of the connected graph; or stratifying a patient's risk grade according to a graphical analysis result of the connected graph.

According to another aspect of the present invention, an apparatus for analyzing pathology patterns of whole-slide images (WSI) based on graph deep learning includes: a WSI compression unit that reads the WSI and compresses the read WSI into a superpatch graph; a graph neural networks (GNN) analysis unit that embeds node features and context features into the superpatch graph through a GNN model and calculating contributions for each node; a biomarker acquisition unit that classifies and groups the superpatch graph according to the contributions for each node, connects the classified and grouped superpatch graph in units of groups to generate connected graphs, normalizes and clusters features of the connected graphs, and acquires environmental graph biomarkers for each group; and a risk analysis unit that performs at least one of a risk area analysis operation of the WSI and a patient risk rating stratification operation based on the environmental graph biomarker for each group.

The present invention enables learning of heterogeneous patterns within cancer tissue in all high-resolution pathological images, which cannot be learned with conventional deep learning models, with a feasible level of GPU memory and computing power through a compressed pathological network.

In addition, by introducing a graph deep learning model that can efficiently learn on a compressed pathological network that cannot be learned with conventional deep learning models, it is possible to learn patterns of various cancer microenvironments in cancer tissues that affect patient's prognosis.

In addition, unlike the conventional deep learning model, which can see only a limited part of pathological images, by an analysis module that can determine the whole pathological tissue associated with patient's prognosis and a method that can extract only significant biomarkers, it is possible to discover meaningful image-based diagnostic biomarkers based on various cancer microenvironmental patterns present throughout high-resolution pathological images.

BRIEF DESCRIPTION OF THE DRAWINGS

FIG. 1 is a diagram for describing a method of analyzing pathology patterns of whole-slide images based on graph deep learning according to an embodiment of the present invention.

FIG. 2 is a diagram for describing a WSI compression step according to an embodiment of the present invention.

FIG. 3 is a diagram for describing a superpatch graph according to an embodiment of the present invention.

FIGS. 4 and 5 are diagrams for describing a GNN analysis step according to an embodiment of the present invention.

FIG. 6 is a diagram for describing a GNN configuration according to an embodiment of the present invention.

FIG. 7 is a diagram for describing a biomarker acquisition step according to an embodiment of the present invention.

FIG. 8A, FIG. 8B and FIG. 8C are a diagram for describing heterogeneous context characteristics according to an embodiment of the present invention.

FIG. 9A, FIG. 9B and FIG. 9C are a diagram for describing an IG group according to an embodiment of the present invention.

FIG. 10 is a diagram for describing a risk analysis step according to an embodiment of the present invention.

FIG. 11 is a diagram for describing a risk heat map and a connected graph according to an embodiment of the present invention.

FIG. 12 is a diagram for describing a risk area according to an embodiment of the present invention.

FIG. 13A, FIG. 13B, FIG. 13C, FIG. 13D, FIG. 13E, FIG. 13F and FIG. 13G are a diagram for describing a correlation between an IG group and a risk according to an embodiment of the present invention.

FIG. 14 is a view illustrating an exemplary computing environment in which one or more embodiments in the present disclosure may be implemented.

FIG. 15A, FIG. 15B and FIG. 15C are a diagram for describing an effect of pathology pattern analysis method of whole-slide images based on graph deep learning of the present invention.

DETAILED DESCRIPTION

Hereinafter, preferred embodiments of the present invention will be described in detail. When it is determined that a detailed description for any known art related to the present invention may obscure the gist of the present invention, the detailed description will be omitted. It should be understood that the singular expression includes the plural expression unless the context clearly indicates otherwise, and it will be further understood that the term "comprise" or "have" used in this specification, specifies the presence of stated features, steps, operations, components, parts, or a combination thereof, but does not preclude the presence or addition of one or more other features, numerals, steps, operations, components, parts, or a combination thereof. In addition, in performing the method or the manufacturing method, each of the processes constituting the method may occur differently from the specified order unless a specific order is explicitly described in context. That is, the respective steps may be performed in the same sequence as the described sequence, be performed at substantially the same time, or be performed in an opposite sequence to the described sequence.

Since the present invention may be variously modified and have several exemplary embodiments, specific exemplary embodiments will be illustrated and be described in detail in a detailed description. However, it is to be understood that the present invention is not limited to a specific exemplary embodiment, but includes all modifications, equivalents, and substitutions without departing from the scope and spirit of the present invention.

The technology disclosed in the present specification is not limited to implementation examples, but may be implemented in other forms. However, exemplary embodiments introduced herein are provided to make disclosed contents thorough and complete and sufficiently transfer the spirit of the present invention to those skilled in the art. In the drawing, in order to clearly express the components of each device, the size of the components, such as width or thickness, is shown somewhat enlarged. When describing the drawings as a whole, it has been described from the observer's point of view, and when one element is referred to as being located on top of another element, this includes all the meanings that one element may be located directly on another element, or additional elements may be interposed between them. In addition, those skilled in the art will be able to implement the spirit of the present invention in various other forms without departing from the technical spirit of the present invention. In addition, like reference numerals in a plurality of drawings denote elements that are substantially the same as each other.

In this specification, the term 'and/or' includes a combination of a plurality of recited items or any one of a plurality of recited items. In the present specification, 'A or B' may include 'A', 'B', or 'both of A and B'.

FIG. 1 is a diagram for describing a method of analyzing pathology patterns of whole-slide images based on graph deep learning according to an embodiment of the present invention.

As illustrated in FIG. 1, the method of the present invention largely includes a whole-slide image (WSI) compression step (S10) of compressing WSI into a superpatch graph, a graph neural networks (GNN) analysis step (S20) of embedding node features and context features into the superpatch graph through a GNN model and calculating contributions for each node and edge, a biomarker acquisition step (S30) of classifying and grouping the superpatch graph according to the contributions for each node, connecting the classified and grouped superpatch graph in units of groups to generate connected graphs, normalizing and clustering features of the connected graphs, and acquiring environmental graph biomarkers for each group, and a diagnostic information extraction step (S40) of extracting and providing diagnostic information on the WSI based on the environmental graph biomarker for each group, and the like.

As such, according to the present invention, it is possible to learn and analyze tumor-environmental context using graph deep learning (TEA graph) which is a GNN-based method of analyzing contextual histopathological features of gigapixel-sized WSI in a semi-supervised manner.

This may compress and represent the WSI with the superpatch, reduces memory capacity for graph representation, and expand an image analysis unit from the existing units of patches to the whole area.

By using all the WSI while maintaining a spatial relationship of each local feature, it is possible to extract the pathological context features through the GNN model, interpret the WSI with an attention score within an edge and an IG method, predict a risk of events such as death and metastasis, and analyze pathological context features associated with prognosis.

In addition, experts may train on the WSI with only label information such as patient status without the need to manually define annotations for a region of interest, and may perform various extractions of interpretable histopathological prognostic markers. In addition, by analyzing risk-related features, it is possible to stratify patients' risk more clearly than the existing histological rating.

Hereinafter, referring to FIGS. 2 to 13, the method of the present invention will be described in more detail.

FIG. 2 illustrates the WSI compression step, FIG. 3 illustrates the superpatch graph, FIGS. 4 and 5 illustrate the GNN analysis step, FIG. 6 illustrates the GNN configuration, FIG. 7 illustrates the biomarker acquisition step, FIG. 8 illustrates the heterogeneous context features, FIG. 9 illustrates an IG group, FIG. 10 illustrates a risk analysis step, FIG. 11 illustrates a risk heat map and a connected graph, FIG. 12 illustrates a risk area, and FIG. 13 is a diagram for describing a correlation between the IG group and risk, respectively.

WSI Compression Step (S10)

S11: Pathological Feature Extraction

First, the WSI is pre-processed with an Otsu threshold to filter out artifacts of the WSI. For example, when a tissue sample is prepared on a pathology glass slide, the WSI includes a tissue sample and a white background that is a glass surface of a pathology glass slide. Accordingly, a patch composed of an Otsu mask having a predetermined percentage (e.g., 75%) or more is selected, so only the tissue sample may be extracted from the WSI and the unnecessary white background may be removed.

As illustrated in FIG. 2, after segmenting the WSI into N small patches of a preset size (e.g., 256×256 pixels) at a preset magnification (e.g., 40-fold magnification), similar patches are defined within the segmented smaller patches.

The pathological features are extracted through pre-trained EfficientNet. For the ccRCC's WSI, the pre-trained EfficientNet for pathology applications is further optimized by performing transfer learning on all the networks for cancer/normal classifiers without layer fixation. To this end, 2,000 small patch images of 256×256 pixels are prepared for each tumor and normal class extracted from the WSI that is manually annotated by a pathologist. The transfer learning is an option for improving the performance of the TEA graph. The reason is that similar results may be obtained in the TCGA data set rather than the ccRCC type without transfer learning.

To define the similar patches, a cosine similarity and a spatial distance (pixel-level L2-norm distance between patches) of features extracted from the pre-trained EfficientNet representing a similarity between images (or similarity between omics) are considered.

To maximize the compression of the similar patches, patches within two patch distances are compared for spatial correlation (up to 24 patches in a 5×5 patch, one patch distance equals to 256 pixels), then the cosine similarity of the patch feature extracted from the pre-trained EfficientNet is measured, and the similar patch is defined when the cosine similarity is lower than the defined threshold.

S12: Generate Superpatch Graph

When the similar patches are defined, an operation of sorting the patches according to the number of similar patches in each patch and then an operation of starting with the patch with the most similar patch and removing the similar patches belonging to the corresponding patch are sequentially performed to generate the superpatch.

After each superpatch is set as a single node in the graph, when the distance between nodes is smaller than a preset distance (e.g., 5 patch distances), the edges between the nodes are generated in consideration of only the spatial distance between the patches, thereby generating the superpatch graph.

S13: Extract Network Feature

The node features for each superpatch are calculated by collecting and averaging, i.e. integrating, the features of small patches in units of superpatches, and the edge features including the geometric structure of the superpatch are calculated through the normalized spatial distance and angle for each patient between the two patches.

GNN Analysis Step (S20)

S21: Construct and Learn GNN Model

In the present invention, for learning and analysis of histopathological context in WSI, GNN, which is a neural network optimized for graph structure processing, is used as illustrated in FIG. 5.

The GNN of the present invention selects GAT as a backbone model to ensure interpretability and maximize learning features. The GAT may differentiate weights of each node when aggregating neighboring features by learning the contributions for each edge. In this case, the contributions for each edge may be calculated as an attention score, etc., and is also used to interpret the importance of each connection between superpatches. Hereinafter, for convenience of description, a case in which the contributions for each edge are calculated through the attention score will be described as an example.

In particular, the attention score calculation method is modified to include the geometric structure features of the edge features, and use a 3-layer GAT with two attention heads (100 dimensions per head) for each layer as the basic structure, which has a receptive field sufficient to capture the environmental features with the GNN. To represent the geometric structure features as learnable parameters, the normalized distances and angles are quantified to numbers 0 to 10 and create lookup tables with the learnable features for the distance and angle.

In addition, to prevent overfitting, LayerNorm is used after activation of each layer, and a parametric rectified linear unit (PReLU) is used as a residual connection between an activation layer and each layer to improve learning features and stability.

For risk score calculation, a combination layer that sums outputs of each GAT layer, a two-layer MLP (800 and 400 dimensions) for post-processing and a final fully connected layer are additionally provided to generate and output a single risk score as the output of the WSI.

In the present invention, the MLP and GAT are implemented using PyTorch and PyTorch Geometric, but it is not necessary to be limited thereto.

S22: Embed Node Feature

To allow the WSI to be processed as end-to-end learning, preprocessing of using a three-layer MLP (e.g., 800, 400, and 200 dimensions) to reduce vector dimensions (e.g., 200 dimensions) of node features for each superpatch is performed.

S23: Embed Context Feature

The outputs $h_i$ of the preprocessing MLP are collected to create inputs h.

$$h=\{h_1,h_2,\ldots,h_N\}, h_i \in \mathbb{R}^{F_n} \qquad \text{[Equation 1]}$$

In this case, N denotes the number of superpatches (nodes), and $F_n$ denotes the number of features in the last layer of the preprocessing MLP.

$$d=\{d_{11},d_{12},\ldots,d_{NN-1},d_{NN}\}, d_{ij} \in \mathbb{R}^{F_n} \qquad \text{[Equation 2]}$$

$$a=\{a_{11},a_{12},\ldots,a_{NN-1},a_{NN}\}, a_{ij} \in \mathbb{R}^{F_n} \qquad \text{[Equation 3]}$$

In this case, distance d and angle a are included as the edge features of the superpatch graph as the learnable parameters, and $F_e$ denotes the number of parameters that can be learned to include the distance and angle features. That is, in the present invention, the distance d and angle a are included in the edge feature as the spatial information between the superpatches, but it is natural that other information besides these information may be additionally used if necessary.

In order to reflect the surrounding environment features that are heterogeneous to the context features, the attention scores $\alpha_{ij}$ for each edge are calculated.

In addition, since it is important to consider the spatial location of each histopathological feature, the attention scores are calculated including the distance and angle features to ensure that location information is transferred between each superpatch.

$$\alpha_{ij} = \frac{\exp\left(LeakyReLU\left(a_s^T W_s h_i + a_r^T W_r h_j + a_d^T W_d d_{ij} + a_a^T W_a a_{ij}\right)\right)}{\sum_{k \in N_i} \exp\left(LeakyReLU\left(a_s^T W_s h_i + a_r^T W_r h_k + a_d^T W_d d_{ik} + a_a^T W_a a_{ik}\right)\right)} \qquad \text{[Equation 4]}$$

In this case, $W_s$, $W_r$, $W_d$, $W_a$ denote initial linear transformations of a source node, a destination node, distance and angle features shared by each layer, $a_s$, $a_r$, $a_d$, $a_a$ denote single-layer feed-forward neural networks for the source node, the destination node, coefficients of the distance and angle features, and Ni denotes a neighboring superpatch of superpatch i in the graph.

Then, the normalized attention coefficient is used to calculate a linear combination of related features. For sufficient representation, the PReLU is used as a non-linear function.

$$h_i' = PReLU\left(\sum_{j \in N_i} (\alpha_{ij} W h_j)\right) \qquad \text{[Equation 5]}$$

In this case, $h_i'$ denotes the final context feature.

S24: Calculate Risk Score

In the present invention, survival prediction is applied to the GAT using a Cox regression loss as a target. The final fully connected layer of the GNN outputs predicted risks $R=\beta^T X$ associated with the input graph, and these risks are input to negative partial log-likelihood of a Cox proportional hazards regression which is the loss function of the model.

$$L(\beta, X) = -\sum_{i \in U}\left(\beta^T X_i - \log \sum_{j \in \Phi_i} e^{\beta^T X_j}\right) \qquad \text{[Equation 7]}$$

In this case, U denotes a list of all patients, and $\phi_i$ denotes a list of patients whose survival time is shorter than that of patient i.

For reference, the GNN model updates hyperparameters to minimize the loss through backpropagation using an Adam optimizer. In this case, it is most preferable to apply the basic parameters of the Adam optimizer with a weight decay coefficient of 0.0005 and use a learning rate scheduler that reduces a learning rate by 0.95 times every steps for faster convergence of the model, but these specific implementation methods may be adjusted in various ways in the future.

S24: Calculate IG Value

Each node has a node feature V of a pre-trained CNN model. For the contribution analysis for each node, a baseline is defined, and the node features extracted from the baseline features needs to be interpolated with the original input node feature V. In this case, the contributions for each node may be calculated by the IG value, etc. Hereinafter, for convenience of description, a case in which the contributions for each node are calculated through the IG value will be described as an example.

The IG value is calculated using an integrated gradients function of a captum (0.4.0) module, and the function uses the node features having zero for the baseline feature.

The IG value is calculated as follows.

$$IG(V^i) = \sum_{k=1}^{l}(V_k^i - V_k^{'i}) \times \sum_{p=1}^{m} \frac{\partial GNN\left[V + \frac{p}{m} \times (V - V')\right]}{\partial V_k^i} \times \frac{1}{m} \qquad \text{[Equation 6]}$$

In this case, $V_k^i$ denotes an i-th node, k denotes a k-th node feature, and m denotes an interpolation step.

After calculating the IG of each node for comparison, all the IG values of the entire WSI are normalized using min-max normalization. A node with a large IG value means that the node has a significant influence on the prediction output (risk). The sign of the IG value indicates the direction of influence, and when the sign of the IG value is negative, it means that a direction in which the node affects the risk is a direction in which the risk decreases.

For validation check, the IG values for the entire data set are collected, and the IG values are grouped into the high 10%, the mid 10%, and the low 10%. These groups are used to characterize the histopathological features of each group.

The median value of each patient's superpatch is selected as the threshold, the IG group is used to divide patients into two groups, and Kaplan-Meier survival analysis is performed to determine the prognostic features of each IG group.

In addition, pairs of high attention (>0.9) and low attention (<0.1) superpatches are extracted, and the correlation between the features of each node obtained from the pre-trained CNN is measured. The fraction of superpatches of the high correlation (>0.8) and the low correlation (<0.2) pairs within the entire high and low attention pairs is calculated. In addition, the pairs of the high and low attention superpatches for each of the high, mid, and low IG groups defined above are extracted. The median feature correlation values within all the high and low attention pairs of each IG group are calculated.

Biomarker Acquisition Step (S30)

S31: Visualize Subgraph

In the present invention, the node represents the superpatch and the edge generates and displays the subgraph representing the connectivity between the superpatches.

In addition, color labels are used to visualize together interpretation metrics such as at least one of the IG and the edge attention. The node color represents the IG value, in which a red node means a high IG value superpatch, and a blue node means a low IG value superpatch. Similarly, the edge color represents the attention score, in which a red edge means a higher weight and a blue edge means a lower weight.

S32: Filter Node

Two models are trained based on the same WSI but on two different clinical data (e.g., cancer-specific survival and metastasis-free survival data), and the IG values are used through two models to observe the risk-related mortality and metastasis area in the same patient.

To extract pathological features correlated with poor prognosis in both clinical data sets, nodes having an IG value difference of less than 0.1 between a survival event and a metastasis event are filtered out. On the other hand, the nodes having the IG value difference of more than 0.5 between the survival event and the transition event are filtered out, which means that the predictive effect of nodes for each event is diametrically opposite.

S33: Extract Environmental Graph Biomarkers Using Connected Graph

After calculating the IG values across the entire data set, the IG values of the high 10%, the mid 10%, and the low 10% as targets for context graph biomarker extraction are grouped.

Among the largest graphs connected within the same group (high, mid, low), only graphs with a preset number of nodes (e.g., 5) or more are defined as the connected graphs, and all the node features of the connected graph are averaged to define the connected graph feature. In the case of the node features, two features, a morphological feature from the pre-trained CNN model and a graphic feature from the trained TEA graph, are connected and used. The graph cluster that represents the largest number of distinguishable clusters is selected.

The features of the connected graphs are normalized in units of groups and the clustering is performed to extract the environmental graph biomarkers of each group. In this case, the clustering may be performed through k-means clustering, but is not necessarily limited thereto.

After visualizing the clustering results using a t-SNE plot, the number of subgraphs in each graph cluster for all patients is counted, the median count value of each graph cluster is measured, and the high count group of each graph cluster is defined as a patient having a higher count value than the median count value of each graph cluster. The low count group represents patients whose count value of each graph cluster is lower than the median value.

The Kapalan-Meier analysis is performed with the high count and lower count groups, and a Kaplan-Meier plot of each cluster is acquired. The differences between regions are measured based on Kaplan-Meier plots of the high and low count groups to evaluate the importance of each subgraph cluster as a prognostic biomarker (P value is calculated with a log-rank test).

All the survival analyses are performed using Python's lifelines package. A cluster having a P value of less than 0.01 is defined as a cluster that can be distinguished from the high/low groups. The graph cluster number with the largest number of identifiable clusters in the high/low group is selected.

Diagnostic Information Extraction Step (S40)

S41: Analyze Risk Area

For analysis for each patch, first, 100 subgraphs are sampled from each graph cluster. Patch-level indexes are created through k-means clustering with patch morphological features from the sampled subgraphs. The patch-level cluster index is assigned to each node of the subgraph in the selected subgraph cluster. Then, each patch-level cluster index pair connected to the edge of the subgraph is counted and normalized with the total number of edges in the subgraph. The patch clusters having high connectivity are selected from the subgraph clusters and the pathological features of the patch-level cluster pairs are interpreted based on the pathological features of each patch-level cluster.

NetworkX is used to visualize each connected graph and labels are designated to the nodes with superpatch labels to characterize label connection patterns of each connected graph. The risk area within the WSI based on the label connection patterns is detected and notified.

S36: Stratify Risk Rating

In order to verify whether the selected subgraph has prognostic power, after calculating the correlation between the graph characteristics of the selected subgraph and other subgraphs belonging to the same graph cluster, the subgraph showing the high correlation (>0.9) between subgraphs having similar pathological characteristics to the selected subgraph is extracted.

In addition, after counting the number of subgraphs that have the high correlation with the selected subgraphs for each patient, patients whose count value is higher than the median value among all patients are defined as the high count group, and patients whose count value is lower than the median value among all patients is defined as a sub-count group.

The Kaplan-Meier plot is acquired in the high and low count groups defined using the count values of the above-described highly correlated subgraph, and based on the Kaplan-Meier plot, the patient's risk rating is stratified into survival, progression, and metastasis.

That is, the present invention enables at least one of the WSI risk area analysis operation and patient risk rating stratification operation is performed based on the environmental graph biomarkers for each group, and the corresponding diagnostic information may be generated and provided.

In addition, the correlation between biomarkers and drug treatment prognosis, the correlation between biomarkers and mutation prediction results, the correlation between biomarkers and gene expression level prediction, and the like may be additionally derived using the same principle as above, and it is natural that various diagnostic tasks such as drug treatment prognosis prediction, mutation prediction, and gene expression level prediction may be additionally performed based on the extracted correlations.

FIG. 14 is a diagram illustrating an apparatus for analyzing pathology patterns of whole-slide images based on graph deep learning according to an embodiment of the present invention.

As illustrated in FIG. 14, an apparatus 100 according to the present invention includes a memory 110 that stores a whole-slide Image (WSI), a WSI compression unit 120 that reads the WSI stored in the memory 110 and compresses the read WSI into a superpatch graph, a GNN analysis unit 130 that embeds node features and context features into the superpatch graph through a graph neural networks (GNN) model and calculates contributions for each node, a biomarker acquisition unit 140 that divides and groups superpatch graphs according to the contributions for each node, connects the divided and grouped superpatch graphs in units of groups to create connected graphs, normalizes and clusters the features of the connected graphs, and acquires environmental graph biomarkers for each group, and a diagnostic information extraction unit 150 that extracts and provides the diagnostic information for the WSI based on the environmental graph biomarkers for each group, and the like.

The apparatus 100 for analyzing pathology patterns configured to implement one or more embodiments described above may include a personal computer, a server computer, a handheld or laptop device, a mobile device (a mobile phone, a PDA, a media player, or the like), a multiprocessor system, a consumer electronic device, a mini computer, a mainframe computer, a computing device including any system or device described above, and the like, but is not limited thereto.

In addition, the apparatus 100 for analyzing pathology patterns may further include input device(s) and output device(s). Here, the input device(s) may include, for example, a keyboard, a mouse, a pen, an audio input device, a touch input device, an infrared camera, a video input device, any other input device, or the like. In addition, the output device(s) may include, for example, one or more displays, speakers, printers, any other output devices, or the like. In addition, an input device or an output device included in another computing device may be used as the input device(s) or the output device(s).

In addition, it may include a communication module enabling communication with other devices. Here, the communications module may include a modem, a network interface card (NIC), an integrated network interface, a radio frequency transmitter/receiver, an infrared port, a universal serial bus (USB) connection, or another interface for connecting to another computing device. Also, the communication module may include a wired connection or a wireless connection.

The respective components of the apparatus 100 for analyzing pathology patterns described above may be interconnected through various interconnections (for example, a peripheral component interconnect (PCI), a USB, a firmware (IEEE 1394), an optical bus structure, and the like) such as a bus, and the like, or be interconnected by a network 1200.

Terms "component," "module," "system," "interface," and the like, used in the present disclosure generally refer to a computer related entity, which is hardware, a combination of hardware and software, software, or software that is being executed. For example, the component may be a process that is being executed on a processor, the processor, an object, an executable structure, an executing thread, a program and/or a computer, but is not limited thereto. For example, both of an application that is being driven on a controller and the controller may be a component. One or more components may exist in the process and/or the executing thread, and the component may be localized on one computer or be distributed between two or more computers.

FIG. 15 is a diagram for describing an effect of pathology pattern analysis method of whole-slide images based on graph deep learning of the present invention.

Five-fold cross-validation is used to evaluate patient-level risk prediction performance of TEA graphs for three different events (survival, progression, and metastasis). The WSI data set of 831 ccRCC patients at Seoul National University Hospital (SNUH) was randomly split into a training set (80%), a validation set (10%), and a test set (10%). Models were trained to predict risk values for patients in all training WSIs and evaluated with test WSIs.

Indexes (C-indexes) of various histopathological data (WHO/ISUP ratings, TNM stages, and other metadata described in methods) provided by pathologists with predicted risk values obtained from TEA graphs were compared.

Although the TEA graph showed limited performance compared to the TNM stage, which includes information that could not be inferred from tissue images, such as metastasis status, it can be seen that the TEA graph performed better than the WHO/ISUP rating for all three events and reached accuracy of 85% in predicting the risk of death of the ccRCC patients.

Combined with data provided by a pathologist, the TEA graph predicted risk values achieved better performance than all other data provided, which may validate the usefulness of the TEA graph. In addition, the TEA graph predicted risk values achieved the highest risk ratios, and showed that the predicted risk scores reflected each patient's probability of event occurrence compared to data provided by other pathologists for all events.

The performance of the TEA graph for patient risk stratification by quantifying THE predicted risk values into four separate groups to generate predictive histopathological ratings was evaluated. The predicted histopathological rating showed improved stratification of patients' risk compared to the WHO/ISUP rating, and in particular, stratified early-stage patients for both survival and metastasis events.

In the present invention, the TEA graph was additionally validated with an external data set and compared its performance with other multi-instance or contextual feature learning models. The WSI data sets of renal (KIRC), breast (BRCA), lung (LUAD and NLST), and cervical (UCEC) patients were trained and evaluated, and compared to the existing models to confirm the usefulness of the TEA graph predictive risk score. In particular, the TEA graph was shown to outperform other contextual feature learning models that do not use position embedded edge features for model training.

Special portions of contents of the present invention have been described in detail hereinabove, and it will be obvious to those skilled in the art that this detailed description is only an exemplary embodiment and the scope of the present invention is not limited by this detailed description. Therefore, the substantial scope of the present invention will be defined by the claims and equivalents thereof.

What is claimed is:

1. A method of analyzing pathology patterns of whole-slide images (WSI) using graph deep learning, the method comprising:

segmenting the WSI into a plurality of small patches and extracting features of each small patch using a pre-trained model;

constructing a superpatch graph by grouping spatially adjacent patches with similar features into superpatches and representing each superpatch as a node, and generating edges between superpatches based on spatial information;

embedding node features and spatial context features of the superpatch graph using a graph neural network (GNN) model, wherein the spatial context features comprise distance and angle between superpatches embedded via a learnable lookup table;

generating a diagnostic score for the WSI using the GNN output;

computing contribution scores for each node and edge in the superpatch graph using an integrated gradients method or another attribution method for interpretability;

clustering nodes with contribution scores to define subgraphs representing environmental graph biomarkers; and providing diagnostic information for the WSI based on the spatial position and graph structure of the environmental graph biomarkers.

2. The method of claim 1, wherein generating the superpatch graph comprises:

segmenting the WSI into N small patches;

generating the superpatch graph according to a similarity of the small patches, and then using the superpatch as a node and connecting between the superpatches with an edge to generate the superpatch graph; and integrating features of the small patches in units of superpatches to calculate node features for each superpatch, and calculating edge features through spatial information between the superpatches.

3. The method of claim 1, wherein the GNN model is configured to:

calculate contributions for each edge between the superpatches based on context features that reflect heterogeneous surrounding environmental conditions; and incorporate spatial information between superpatches to promote location information transfer between the superpatches.

4. The method of claim 2 or 3, wherein the spatial information includes a distance and an angle between the superpatches.

5. The method of claim 1, wherein embedding the node features and the spatial context features using the GNN model:

reducing a vector dimension of the node features for each superpatch;

embedding the node features and the context features in the superpatch graph through the GNN model;

extracting the context features through the GNN model and calculating the diagnostic score; and calculating the contributions for each node, wherein a contribution between adjacent superpatches, including spatial information between the superpatches, is calculated to reflect a heterogeneous surrounding environment feature to the context feature.

6. The method of claim 1, further comprising:

generating and displaying subgraphs by connecting between the superpatches with the edge using the superpatch as a node and additionally guiding at least one of contributions for each node and contributions for each edge;

classifying and grouping the subgraphs according to the contributions for each node, and then connecting the classified and grouped subgraphs in the units of groups to generate the connected graphs, and averaging all the node features in the connected graph to define connected graph features; and normalizing and clustering all the connected graph features within the same group to extract biomarkers of each group.

7. The method of claim 6, wherein, in the step of defining the connected graph features, only graphs having a predetermined number of nodes or more among largest connected graphs within the same group are defined as the connected graph.

8. The method of claim 1, wherein the diagnostic information is generated by:

detecting and notifying the risk in the WSI based on a connectivity analysis result of the connected graph; or stratifying a patient's risk grade according to a graphical analysis result of the connected graph.

9. An apparatus for analyzing pathology patterns of whole-slide images (WSI) using graph deep learning, the apparatus comprising:

a WSI compression unit, comprising a processor and memory, configured to segment the WSI into a plurality of small patches, extract patch-level features using a pretrained model, and compress the patches into a superpatch graph by grouping spatially adjacent and feature-similar patches into superpatches, each represented as a node;

a graph analysis unit, configured to embed node features and spatial context features of the superpatch graph using a graph neural network (GNN), wherein the context features include distance and angle between superpatches;

a contribution analysis unit, configured to compute contribution scores for each node and edge using an integrated gradients method or another attribution method for interpretability;

a graph grouping unit, configured to classify and group superpatches based on their contribution scores to identify connected subgraphs representing environmental graph biomarkers;

a biomarker acquisition unit, configured to extract environmental graph biomarkers by analyzing spatial topology of high-contribution subgraphs; and a diagnostic information extraction unit, configured to generate and provide a diagnostic score, based on the identified graph biomarkers and their spatial distribution in the WSI.

\* \* \* \* \*

16